(12) United States Patent
Shah et al.

(10) Patent No.: US 11,746,443 B1
(45) Date of Patent: Sep. 5, 2023

(54) POLYCAPROLACTONE-BASED FIBERS AND IMPLANTS INCLUDING SAME

(71) Applicant: Cook Biotech Incorporated, West Lafayette, IN (US)

(72) Inventors: Bhavin Shah, West Lafayette, IN (US); Benjamin Kline, Brookston, IN (US); Rhonda Peck, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 210 days.

(21) Appl. No.: 16/893,777

(22) Filed: Jun. 5, 2020

Related U.S. Application Data

(60) Provisional application No. 62/858,560, filed on Jun. 7, 2019.

(51) Int. Cl.
| | |
|---|---|
| *D01F 6/62* | (2006.01) |
| *A61L 29/06* | (2006.01) |
| *A61L 31/06* | (2006.01) |
| *D02J 1/20* | (2006.01) |
| *A61L 27/18* | (2006.01) |

(52) U.S. Cl.
CPC ............. *D01F 6/625* (2013.01); *A61L 27/18* (2013.01); *A61L 29/06* (2013.01); *A61L 31/06* (2013.01); *D02J 1/20* (2013.01); *D10B 2331/041* (2013.01); *D10B 2401/061* (2013.01); *D10B 2509/00* (2013.01)

(58) Field of Classification Search
CPC .......... A61L 27/18; A61L 29/06; A61L 31/06; D01F 6/625
See application file for complete search history.

(56) References Cited

U.S. PATENT DOCUMENTS

| | | |
|---|---|---|
| 3,361,859 A | 1/1968 | Cenzato |
| 2008/0061467 A1 | 3/2008 | Iwata et al. |

OTHER PUBLICATIONS

Kim et al., ("Surface Modification of Melt Extruded Poly(-caprolactone) Nanofibers: Toward a New Biomaterial Scaffold" in ACS Macro Letters, Jun. 6, 2014). (Year: 2014).*

Azimi et al., "Poly(-caprolactone) Fiber: An Overview" in Journal of Engineered Fibers, vol. 9, Issue 3, 2014, pp. 74-90. (Year: 2014).*

Molloy et al. "Factors influencing the small-scale melt spinning of poly(-caprolactone) monofilament fibers" in Polymer International, vol. 52, pp. 1175-1181, 2003. (Year: 2003).*

Gisela C. C. Mendes et al., "Ethylene oxide sterilization of medical devices: A review," in American Journal of Infectious Control, Nov. 2007; 35(9):574-581 (Year: 2007).*

(Continued)

*Primary Examiner* — Blessing M Fubara
(74) *Attorney, Agent, or Firm* — Woodard, Emhardt, Henry, Reeves & Wagner, LLP

(57) ABSTRACT

A polymeric material fiber includes a polymeric material which is a homopolymer of caprolactone or a copolymer of at least 90% by weight of caprolactone and one or more additional monomers. An implantable mesh includes this fiber alone or combined with one or more additional fiber materials. Methods for treating patients involve implanting the fiber material, for example incorporated in a mesh.

32 Claims, 10 Drawing Sheets

(56) References Cited

OTHER PUBLICATIONS

Kaffashi et al. "Poly(e-caprolactone)/triclosan loaded polylactic acid nanoparticles composite: A long-term antibacterial bionanocomposite with sustained release" in International Journal of Pharmaceutics, 508 (2016) 10-21. (Year: 2016).*

"A study of the impact of ethylene oxide sterilizing modes on properties of glycolactic sutures". Tomsk State University Journel, 2014 No. 3.

Abedalwafa et al. "Biodegradable Poly-Epsilon-Caprolactone (PCL) for Tissue Engineering Applications: A Review", Rev. Adv. Mater. Sci. 34 (2013), pp. 123-140.

Azimi et al. "Poly (e-caprolactone) Fider: An Overview", Journal of Engineered Fibers and Fabrics, vol. 9, Issue 3, 2014.

Baylon et al. "Past, Present and Future of Surgical Meshes: A Review", Membranes 2017, 4, 47.

Catanzano et al., "Melt-spun bioactive sutures containing nanohybrids for local delivery of anti-inflammatory drugs", Materials Science and Engineering C 43 (2014) pp. 300-309.

Chu "Materials for absorbable and nonabsorbable surgical sutures", Biotextiles as Medical Implants, 2013, 1 pg.

Deeken et al. "Characterization of the Mechanical Strength, Resorption Properties, and Histologic Characteristics of a Fully Absorbable Material (Poly-4-hydroxybutyrate- PHASIX Mesh) in a Procine Model of Hernia Repair", ISRN Surgery, vol. 2013, Article ID 238067, 12 pgs.

Gardyne et al. "The application of co-melt-extruded poly(e-caprolactone) as a controlled release drug delivery device when combined with novel bioactive drug candidates: Membrane permeation and Hanson dissolution studies", Results in Pharma Sciences 1 (2011) pp. 80-87.

Haji et al. "The Effect of Hot Multistage Drawing on Molecular Structure and Optical Properties of Polyethylene Terephthalate Fibers", Material Research, 2012; 15(4): 554-560.

Hayashi et al. "Studies on Biodegradable Poly(Hexano-6-Lactone) Fibers. Part 3. Enzymatic Degradation in Vitro", Pure Appl. Chem., vol. 74, No. 5, pp. 869-880, 2002.

La Mantia et al. "Effect of cold drawing on mechanical properties of biodegradable fibers", J. Appl. Biomater Funct Mater 2017, 15(1): e70-e76.

Mochizuki et al. Studies on Biodegradable Poly(Hexano-6-Lactone) Fibers 1. Structure and Properties of Drawn Poly (Hexano-6-Lactone) Fibers. Pure & Appl. Chem. vol. 69, No. 12, pp. 2567-2575, 1997.

Mochizuki et al. "Studies on Biodegradable Poly(Hexano-6-Lactone) Fibers. Part 2: Environmental Degradation", Pure Appl. Chem., vol. 71, No. 11, pp. 2177-2188, 1999.

Molloy et al. D-11 Kinetic Studies of the Ring-Opening Bulk Polymerization of e-Caprolactone by Dilatometry (Session: Polymer/Wear), Journal of Solid Mechanics and Materials Engineering, vol. 1, No. 4, 2007, pp. 613-623.

Molloy et al. "Factors influencing the small-scale melt spinning of poly (?-caprolactone) monofilament fibers", Polymer International, Jul. 2003.

Scott et al. "Evaluation of a fully absorbable poly-4-hydroxybutyrate/absorbable barrier composite mesh in a porcine model of ventral hernia repair", Surg.Endose (2016) 30:3691-3701.

Speranza et al. "Characterization of the Polycaprolactone Melt Crystallization: Complementary Optical Microscopy, DSC, and AFM Studies", The Scientific World Journel, vol. 2014, Article ID 720157, 9 pgs.

Williams et al. "Poly-4-hydrexybutyrate (P4HB): a new generation of sesorbable medical devices for tissue repair and regeneration", Biomedizinische Technik/Biomedical Engineering, Jun. 13.

* cited by examiner

POLYCAPROLACTONE-BASED FIBERS AND IMPLANTS INCLUDING SAME

REFERENCE TO RELATED APPLICATIONS

This application is a non-provisional application claiming the benefit of U.S. Provisional Patent Application No. 62/858,560, filed Jun. 7, 2019, pending, which is incorporated herein by reference.

BACKGROUND

The present disclosure relates generally to implantable materials, and in some aspects to implantable polycaprolactone-based fiber materials and implants, for example surgical meshes, that contain the fiber materials potentially in combination with other fiber materials.

Implantable devices or materials constituted of or containing bioabsorbable fibers have become important for patient care. For instance, surgical meshes containing bioabsorbable fibers have been widely used for surgical procedures such as hernia repair, pelvic floor repair, urethral slings, and many others.

Bioabsorbable fibers, and surgical meshes or other devices containing them, need to be cost effective while exhibiting suitable physical properties such as strength, flexibility and handling and also need to be beneficially biocompatible and provide desirable degradation and tissue response profiles after implantation in a patient. In this vein, there are needs for improved and/or alternative bioabsorbable fiber materials and devices containing them, and related methods of preparation and use. In several aspects, the embodiments of the present disclosure address these needs.

SUMMARY

It has been discovered that polymeric fibers with beneficial strength and other properties can be prepared from purely or highly polycaprolactone-based materials. The strong fibers can demonstrate advantageous rates of degradation when exposed to aqueous environments, such as those which occur after implantation in a patient, which preferably provide prolonged strength to the fibers and devices containing them.

Accordingly, certain embodiments herein provide melt extruded, oriented polymeric material fibers, wherein the polymeric material is a homopolymer of caprolactone or a copolymer of at least 90% by weight of caprolactone and one or more additional monomers. In some forms, the polymeric material fiber has been stress hardened by cold drawing. The fiber can have a tensile strength greater than about 450 megapascals (MPa) and typically in the range of 450 MPa to 650 MPa. The fiber can have an elongation at break in the range of 45% to 65%, and/or an elastic modulus in the range of 750 MPa to 1200 MPa. The fiber can have an average diameter in the range of about 0.01 mm to about 4 mm. The homopolymer or the copolymer of the fiber can be a linear polymer. The tensile strength of the fiber can decrease less than 20% after immersion in phosphate buffered saline for 6 months. In preferred forms, the polymeric material is a homopolymer of caprolactone and/or has a weight average molecular weight in the range of about 10000 kDa to about 150000 kDa. The fiber can be prepared by a method comprising melt extruding the polymeric material to form an extrudate, allowing the extrudate dwell time to solidify, and drawing the extrudate. The fiber can be sterilized, for example by exposure to ethylene oxide gas (EO) or irradiation.

Additional embodiments herein provide medical devices that include one or more melt extruded, oriented polycaprolactone-based polymeric fibers, such as disclosed herein. In preferred aspects, the medical devices are surgical meshes. Such a mesh can be a knitted mesh, woven mesh, or nonwoven mesh comprising one or more of the melt extruded, oriented polycaprolactone-based polymeric fibers. The mesh can have a density in the range of about 30 to about 100 g/m$^2$ and/or an average pore size in the range of about 0.25 square micrometers to about 2500 square micrometers. The mesh can have a tensile strength of greater than about 30 N/cm and/or a ball burst strength of greater than about 50 N/cm. The mesh can be constituted at least 50% by weight of the melt extruded, oriented polycaprolactone-based polymeric material fiber(s). In some forms, the melt extruded, oriented polycaprolactone-based polymeric material fibers can be the only fibers of the mesh. In other forms, the melt extruded, oriented polycaprolactone-based polymeric material fibers can be included in the mesh along with one or more additional, different fibers. The mesh can be combined with another material, for example a sheet material which in some forms can be a sheet or sheets of decellularized extracellular matrix tissue, in an implant device.

In further embodiments, provided are methods for making a mesh device, for example any mesh device specified herein. The method includes weaving, knitting, or otherwise associating (e.g. as in the preparation of a nonwoven mesh) one or more of the melt extruded, oriented polymeric material fibers of the caprolactone homopolymer or copolymer disclosed herein, alone or in combination with one or more other different fibers, to form a mesh. In some embodiments, in a further step, the mesh is combined with (e.g. attached to) another material, for example a sheet material which in some forms can be a sheet or sheets of decellularized extracellular matrix tissue, to form an implant device. The mesh device or implant device including it can be sterilized, for example by exposure to ethylene oxide gas (EO) or irradiation.

Still further embodiments herein provide methods for making a melt extruded, oriented polymeric material fiber. The methods include melt extruding a polymeric material which is a homopolymer of caprolactone or a copolymer of at least 90% by weight of caprolactone and one or more additional monomers, to form an extrudate. The extrudate is drawn (i.e. stretched) to form the melt extruded, oriented polymeric material fiber. The drawing step can stress harden the fiber. The drawing step can elongate the extrudate by at least 600%. The melt extruding can include extruding the polymeric material through an opening having a diameter in the range of about 0.2 mm to about 3 mm. The drawing can increase the crystallinity of the polymer material by at least 0.5% (e.g. in the range of 0.5% to 10%), can provide a drawn fiber having an increased tensile strength as compared to the extrudate, and/or can provide a drawn fiber with a diameter that is decreased by at least 40% as compared to the extrudate, and in some embodiments in the range of about 40% to about 60%. The melt extruding can be conducted with the polymeric material at a temperature in the range of about 80° C. to about 140° C. The extrudate can have an average diameter in the range of about 0.3 mm to about 4 mm. The method can also include maintaining the extrudate for a dwell time to allow the polymeric material to crystallize prior to the drawing step, potentially to provide a semi-crystalline polymeric material with a crystallinity in the range of about 35% to about 45%. The drawing can be conducted with the polymeric material at a temperature below 40° C., for example in some forms with the polymeric material at a temperature in the range of about 10° C. to about 30° C. In addition or alternatively, the drawing can be conducted with the polymeric material at a temperature that is at least 10° C. below, or at least 20° C. below, the melting temperature for the polymeric material.

Other embodiments herein provide methods for treating human or other animal patients that include implanting in a patient a melt extruded, oriented polycaprolactone-based polymeric material fiber as disclosed herein, or a device including one or more such fibers.

Still further embodiments, as well as features and advantages of embodiments herein, will be apparent to those of skill in the pertinent field from the disclosures herein.

DETAILED DESCRIPTION

Figure 1:
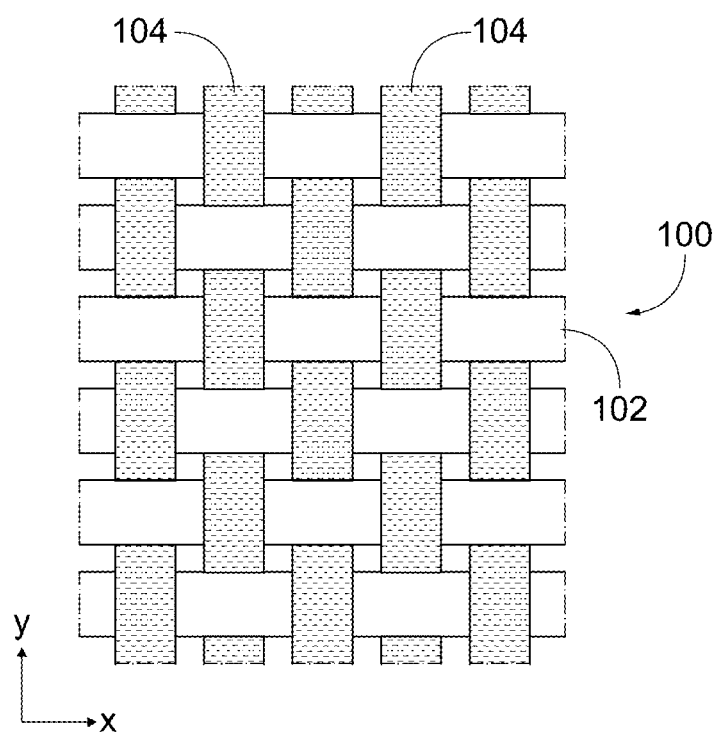
FIG. 1 illustrates the configuration of one embodiment of a mesh incorporating fibers as disclosed herein.

Reference will now be made to embodiments, some of which are illustrated in the drawings, and specific language will be used to describe the same. It will nevertheless be understood that no limitation of the scope of the disclosure is thereby intended. Any alterations and further modifications in the described embodiments and any further applications of the principles as described herein are contemplated as would normally occur to one skilled in the art to which this disclosure relates.

As discussed above, embodiments of this disclosure relate to melt extruded, oriented polymeric material fibers, medical devices incorporating such fibers, and related methods of making and using the fibers and medical devices.

The polymeric material of the melt extruded, oriented fibers is a homopolymer of caprolactone or a copolymer of at least 90% by weight of caprolactone and at most 10% by weight of one or more other monomers (such a polymeric material is referred to herein as a "polycaprolactone-based polymeric material"). The one or more other monomers can be biodegradable, non-biodegradable, or mixtures thereof. Examples of biodegradable monomers that may be used along with caprolactone are glycolic acid, a glycolide, lactic acid, a lactide, p-dioxanone, valerolactone and other lactones derived from linear aliphatic hydroxycarboxylic acids, α-hydroxybutyric acid, ethylene carbonate, ethylene oxide, propylene oxide, propylene carbonate, malic acid ester lactones, succinic acid, adipic acid and other linear aliphatic dicarboxylic acids, and linear aliphatic diols such as butanediol and hexanediol. Examples of non-biodegradable monomers that may be used along with caprolactone are propylene, ethylene, acrylic acid, amides, and fluorinated monomers such as tetrafluoroethylene.

The caprolactone homopolymer or copolymer can be made by conventional methods for the polymerization of ε-caprolactone, potentially with other monomer(s). Conventional polymerization techniques that can be used are described for example in U.S. Pat. No. 4,190,720. Suitable polycaprolactones are also commercially available, e.g. from Polysciences, Inc. of Warrington, PA, USA. The caprolactone homopolymer or copolymer can have a weight average molecular weight of about 10,000 to about 150,000 kDa, more preferably about 40,000 to 100,000 kDa. In certain preferred forms, a caprolactone homopolymer is used and has a molecular weight of about 80 kDa.

In an illustrative process for producing a polycaprolactone-based polymeric material filament according to the present invention, a polycaprolactone-based polymeric material is used as a starting material. The polycaprolactone-based polymeric material is melt extruded, for example at an extrusion temperature at or above its melting temperature, e.g., at a temperature in the range of about 60° C. to about 100° C. for certain polycaprolactone-based polymeric materials. The extrusion temperature can in some embodiments be at least 1° C. above, or at least 3° C. above, the melting temperature of the polymeric material, typically no greater than about 50° C. above the melting temperature of the polymeric material and in some forms no greater than about 10° C. above the melting temperature of the polymeric material. Conventional extrusion equipment and processing can be used. Then, the melt extruded polycaprolactone-based polymeric material can be allowed to cool and solidify, for example in air or optionally by immersion in a liquid bath of water or any other suitable liquid. In some preferred forms, the cooling is conducted in a fluid (gas or liquid) at a temperature in the range of about 20° C. to about 30° C., e.g. in air at room temperature. Such a moderate temperature fluid can provide a relatively slow cooling of the polymeric material. After solidification, the polymeric material can be semi-crystalline, for example having a crystallinity of at least about 20% and in some forms in the range of about 35% to about 45%. After solidification, the polycaprolactone-based polymeric material is stretched (i.e. drawn) at a temperature below its melting temperature, for example at least 10° C. below its melting temperature, more preferably at least 20° C. below its melting temperature.

In some embodiments, the polycaprolactone-based polymeric material will have a melting temperature of at least about 50° C. (e.g. in the range of about 50° C. to about 100° C.), or in some forms at least about 60° C. (e.g. in the range of about 60° C. to about 80° C.), and the stretching will be conducted at a temperature below about 30° C. (e.g. in the range of about 0° C. to about 30° C. or about 15° C. to about 30° C.). In some forms, the stretching can increase the crystallinity of the polycaprolactone-based polymeric material, for example by about 1% to about 10%, and/or can provide a drawn fiber with a tensile strength greater than that of the extrudate, and/or can provide a drawn fiber with a diameter less than that of the extrudate, and/or can provide a drawn fiber with an elongation at break less than that of the extrudate.

The stretching can be performed as a single operation or in multiple successive operations. The stretching can provide an overall stretch ratio (the ratio of the unstretched extrudate to the final stretched fiber) of 5 times (i.e. 500%) or higher, typically in the range of 5 to 10 times (i.e. 500% to 1000%). In addition or alternatively, the stretching can be performed under conditions such that the polycaprolactone-based polymeric material is stress hardened, as can be achieved by stretching the polymeric material beyond its inflection point. The stretching can be terminated prior to breakage of the polycaprolactone-based polymeric material and when the material is in its stretch hardening phase. In addition or alternatively, the stretching can reduce the diameter of the extrudate by at least about 40%, or at least about 50%, and in some forms in the range of 40% to 60%.

In some forms, the stretching is conducted at a strain rate in the range of about 50 mm/minute to about 150 mm/minute, preferably about 75 mm/minute to about 125 mm/minute. Without intended to be limited by any theory, is it believed that the use of such moderate strain rates will allow the polymeric molecules to seek additional rearrangements after an initial dimensional alignment has occurred.

The polycaprolactone-based polymeric material fiber disclosed herein can be characterized by a tensile strength of at least 400 MPa, preferably at least 450 MPa, in each case optionally not exceeding about 650 MPa, and/or a tensile elongation at break of about 40% to about 80%, more preferably about 45% to about 60%. In addition or alternatively, the drawn polycaprolactone-based polymeric material fiber can have an elastic modulus of greater than about 700 MPa, more preferably greater than about 800 MPa, and in some forms in the range of about 700 MPa to about 1200 MPa. Unless otherwise stated herein, values for tensile strength, tensile elongation at breakage, elastic modulus, or other strength or physical properties, are values for the polycaprolactone-based polymeric material fiber, or a device including it, in a dry condition.

The diameter of the polycaprolactone-based polymeric material fiber is preferably in the range of about 0.01 to about 4 mm, more preferably about 0.02 to about 3 mm, and even more preferably about 0.02 to about 1 mm. For uses as suture material, the polycaprolactone-based polymeric material fiber will typically have a diameter in the range of about 0.01 to about 0.8 mm.

The polycaprolactone-based polymeric material fiber can have a crystallinity at or above 35%, and in some forms in the range of 35% to about 50%. This level of crystallinity can result from an increase in crystallinity of the drawn or stretched fiber as compared to the unstretched extrudate from which it was formed.

The polycaprolactone-based polymeric material fiber can have specified properties relating to degradation in aqueous environments, e.g. aqueous saline or bodily fluid environments. In some forms, the polycaprolactone-based polymeric material fiber will exhibit a loss in tensile strength following immersion for a period in a 0.9% phosphate buffered saline solution, pH 7.4, at 37° C., as set forth in the Table below.

TABLE

| Duration of immersion | Loss in Tensile Strength |
| --- | --- |
| 1 month | Less than 5%, or less than 3%. |
| 6 months | Less than 20%, or less than 10%. |
| 12 months | Less than 30%, or less than 20%. |

These values for loss in tensile strength can be obtained comparing initial values for specimens equilibrated in the phosphate buffered sodium chloride solution (e.g. for 60 minutes) to values for specimens after the indication duration of immersion, for example in accordance with ASTM 1635-16, "Standard Test Method for in vitro Degradation Testing of Hydrolytically Degradable Polymer Resins and Fabricated Forms for Surgical Implants".

The polycaprolactone-based polymeric material fiber according to the present disclosure can entrain and/or be coated with one or more bioactive agents, for example drug compounds. In some forms, one or more drug compounds can be in mixture with the molten polymeric material during the melt extrusion process, and thereby become entrained in the extruded and drawn polymeric material fiber. In preferred forms the relatively moderate to low melting temperature of the polycaprolactone-based polymeric material can be beneficial to the range of drug compound(s) or other bioactive agent(s) to be melt-entrained in the fiber while maintaining the thermal stability of the drug compound(s) or other bioactive agent(s). Illustrative classes of drug compounds that may be melt-entrained in the polymeric fiber include antimicrobial compounds and analgesic compounds.

The polycaprolactone-based polymeric material fiber according to the present disclosure may be used in a wide variety of applications, including medical applications. Medical applications include use as or in an implantable material or device, including for example a medical textile, tube, surgical mesh, hernia mesh, breast reconstruction mesh, mastopexy mesh, pericardial patch, anti-adhesion patch, cardiovascular patch, guided tissue regeneration patch, sling, monofilament suture, multifilament suture, ligament repair device, tendon repair device, meniscus repair device, cartilage repair device, nerve guide, stent, vascular graft, or dura repair device.

In some preferred forms, the present disclosure provides meshes that incorporate one or more polycaprolactone-based polymeric material fibers as disclosed herein. One embodiment of a mesh is illustrated in FIG. 1. The mesh 100 is a plain weave mesh including a first plurality of filaments 102 positioned next to one another and extending along the width of the mesh in direction x, and a second plurality of filaments 104 positioned next to one another and extending along the length of the mesh in direction y, and woven through the filaments 102 of the first plurality of filaments. Such a plain weave mesh can be manufactured by any well known technique, such as a shuttle loom, Jacquard loom or Gripper loom. In these looms the process of weaving remains similar, the interlacing of two systems of filaments at right angles. This lacing can be simple as in a plain weave (FIG. 1) where the lacing is over one and under one. The plain weave can be changed to a more elaborate construction, for example a twill weave or satin weave, which will provide different features to the mesh.

Figure 2:
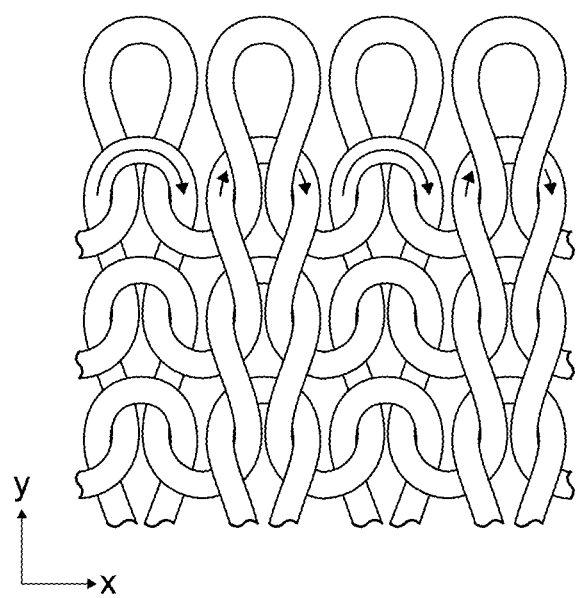
FIG. 2 illustrates the configuration of another embodiment of a mesh incorporating fibers as disclosed herein.

It is also possible to create meshes using other manufacturing techniques. These meshes can be constructed by knitting, which is a process of making a mesh with a single fiber or set of fibers moving in only one direction. In weaving, two sets of fibers cross over and under each other. In knitting, the single fiber is looped through itself to make the chain of stitches. One method to do this is described as weft knitting, an example of which is shown in FIG. 2. In this construction the fibers are introduced from the side (the x direction) or horizontally opposite to the direction of growth of the mesh (the y direction).

Another method of weaving is a leno weave. In this construction two warp yarns are twisted and the fill yarns are passed through the twist. It will be clear to those skilled in the art that additional variations of the basic weaves such as, sateen weaves, antique satin, warp faced twills, herringbone twills and tri-axially woven meshes as well as others can be used to create woven meshes contemplated herein.

Another method for knitting a mesh is warp knitting. In this method the fibers are introduced in the direction of the growth of the mesh (in the y direction). In this type of mesh the fibers are looped vertically and also to a limited extent diagonally, with the diagonal movement connecting the rows of loops.

Different types of warp knits can be used to construct a mesh for this purpose, such as Tricots, Raschel and Cidega knits. In producing a warp knit with a Raschel knitting machine, multiple variations in construction can be achieved. As well, there is a technique in Raschel knitting that uses a "fall plate" that can produce a structure that will look more like a woven mesh. A single fiber is carried across a number of warps in a horizontal or diagonal direction. This fiber connects and holds the warps together.

A further method of constructing a mesh includes combining weaving and knitting. This method is sometimes referred to as "Co-We-Nit". In this construction, knitting and weaving can be combined to create meshes with greater dimensional stability than conventional knits but with some of the properties of knitted goods.

In yet other embodiments, the mesh can have a non-woven construction. In a non-woven construction preparative process, fibers can be mechanically deposited to form a mat. The mat can then be treated to provide integrity. The treatment can include manipulation of the filaments to entangle them or melt them together, or bind them with an adhesive or curing resin.

In some embodiments, the fibers of the present disclosure can constitute all of the fibers of a mesh, e.g. any of those disclosed herein. In other embodiments, the fibers of the present disclosure can constitute only a portion of the fibers of the mesh, with one or more other types of fibers (some or all of which can also be bioabsorbable) also included in the mesh. The fibers incorporated in these or other meshes herein can be constituted at least 50% by weight of the polycaprolactone-based polymeric material fibers disclosed herein, or in some forms entirely of the polycaprolactone-based polymeric material fibers disclosed herein. When other fiber(s) are included in the mesh, the other fiber(s) can all be bioabsorbable, all be non-bioabsorbable, or can be a combination of bioabsorbable and non-bioabsorbable fibers. Preferred bioabsorbable fibers that can be used in combination with the polycaprolactone-based polymeric material fibers disclosed herein include polyglactin fibers, polydioxanone fibers, polylactic acid fibers, polylactide fibers, and polylactic acid/glycolic acid copolymer fibers. Non-bioabsorbable fibers that can be used in combination with the polycaprolactone-based polymeric material fibers disclosed herein include polypropylene fibers, polyester fibers, polyethylene fibers, acrylic fibers, polyamide fibers, aramid fibers, fluropolymer fibers, and flurocarbon fibers.

Where the mesh includes a combination of bioabsorbable fibers of the present disclosure with another bioabsorbable fiber, such other bioabsorbable fiber can bioabsorb more quickly, or more slowly, than the fibers of the present disclosure. Examples of fibers that can bioabsorb more quickly than the fibers of the present disclosure include polygalactin, Vicryl polydioxanone, PDS Monocryl, polylactic acid, Panacryl, and regenerated cellulose fibers.

In certain embodiments, the mesh can include the polycaprolactone-based fibers of the present disclosure extending exclusively or predominantly in a first (e.g. x) direction of the mesh, and different fibers extending in a second (e.g. y) direction of the mesh, where the different fibers bioabsorb more quickly than the polycaprolactone-based fibers of the present disclosure. In this manner, the mesh can exhibit a modified strength profile over time after implantation, where the mesh retains a higher tensile strength in the first (x) direction over time as compared to the second (y) direction. Such meshes can be useful, for example, in tissue support medical applications where a more prolonged tensile strength in the first direction is beneficial to patient healing.

In addition to selecting different materials, the diameter of the fibers can be selected to alter the physical properties of a mesh. Increasing the diameter of a fiber can increase the absorption time, whereas decreasing the diameter of a fiber can decrease the absorption time.

Meshes of the present disclosure can exhibit beneficial physical and mechanical properties. In some forms, the mesh can have a tensile strength of greater than about 30 N/cm, typically in the range of about 30 N/cm to about 200 N/cm; can have a suture retention strength of greater than about 20 N, typically in the range of about 20 N to about 70 N; and/or can have a ball burst strength of greater than about 50 N/cm, typically in the range of about 50 N/cm to about 600 N/cm. The mesh can have a density in the range of about 30 to about 100 $g/m^2$ and/or an average pore size in the range of about 0.25 square micrometers to about 2500 square micrometers.

The meshes disclosed herein can also be combined with other devices or materials in implant device constructions. For example, the meshes can be laminated with or otherwise attached to sheet materials, for example decellularized extracellular matrix tissue sheet materials, optionally submucosal decellularized extracellular matrix tissue materials, to provide tissue support implants (e.g. hernia repair devices). In some forms, the meshes can be sandwiched between first and second decellularized extracellular matrix tissue sheet materials, for example as described in U.S. Pat. No. 9,295,757, which is herein incorporated by reference in its entirety.

The polycaprolactone-based polymeric material fiber(s), or devices such as meshes incorporating them, can be sterilized. Suitable sterilization processes include exposure to ethylene oxide gas (EO) or to radiation such as, for example, gamma radiation or electron beam radiation. In accordance with the disclosure herein, the sterilization technique can be controlled to prevent or minimize change to the polymeric material fiber(s). For example, the sterilization can be controlled to result in no more than a 10% decrease in the tensile strength of the fiber(s).

In some aspects, the polycaprolactone-based polymeric material fiber(s), or devices such as meshes incorporating them, are terminally sterilized. For these purposes, the fiber(s) or devices such as meshes incorporating them can be enclosed within a package, e.g. within a film, pouch, foil, tray or other enclosure, and the packaged fiber(s) or devices can then be subjected to EO or radiation, e.g. any of those discussed above. It will be understood in these techniques that the package will be permeable to the sterilization agent utilized. Such terminally sterilized products represent additional embodiments of the present disclosure.

The following specific Experimental is provided to promote a further understanding of aspects of the present disclosure. It will be understood that this Experimental is illustrative, and not limiting, in nature.

EXPERIMENTAL

Terms and Definitions

Glass transition temperature (Tg): the temperature range of the short and reversible transition period where an amorphous material transits from hard/brittle state into a viscous/rubbery state. Tg is always lower than the Tm of the amorphous material.

Efiber: The extruded microfiber resulting from the Extrusion process.

Sfiber: The Efiber which has cold-stretched using the in-house developed calibrated method to obtain a thinner fiber with comparable mechanical strengths to polydioxanone[4]. This is essentially the Efiber stress-hardening region, which undergoes irreversible deformation during the cold-stretching process.

Equilibrium region (of Efiber): The equilibrium region of the extrusion process. This is the extruded material (extrudate) collected after approx. 15 min of the batch process. Before the equilibrium region, the Efiber is thicker and rugged in appearance. After the equilibrium region, the Efiber is thinner. To obtain the equilibrium region, 1.5 m is discarded from each end of the Efiber.

Tensile stress: The tensile stress is obtained by dividing the tensile force required to break a material, by the materials cross-sectional area. It has units of $N/mm^2$. The term tensile stress is interchangeably used with tensile strength.

% strain: the percentage of extension prior to the material's yield point.

Elastic Modulus: This is obtained by dividing the tensile stress by % strain. It is an indicator of how stiff a material is. For example, metal has a high Elastic Modulus while that of rubber is low. When the same force is applied, on metal and rubber, metal will deflect (extend) lesser compared to rubber.

1. Materials and Methods 1.1. Materials and Equipment

Polycaprolactone (molecular weight: 80,000 Da) pellets were purchased from Polysciences, Warrington, Pa. The PCL pellets as received had been unitized into foil pouches, using Nitrogen sealed, and stored at 4° C. for future use.

A Filabot extruder with a single screw was used for all extrusion processes in the current study. The barrel length and inner diameter (ID) were 23.0 cm, and 1.5 cm respectively. The nozzle had an inner diameter of 1.1 cm. The manufacturer specified die opening diameter of 0.05 cm was used as a constant in the experimentation. The extrusion processes were run essentially in a batch mode.

1.2 Methods 1.2.1 Cleaning the Extruder

At the beginning of each run, the screw and barrel were thoroughly cleaned using dichloromethane (DCM).

1.2.2 Pre-heating the Extruder

After cleaning, the extruder was switched on, set at 80° C. and heated for approx. 1 hr to reach thermal equilibrium. Extruder temperature settings of 80° C., 90° C., and 100° C. were tested, and no clogging issues were observed at these settings. 80° C. was selected for continuing runs since it was the lower of these temperatures and yet enabled a consistent extrudate throughput. It should be reiterated that all of the above temperature settings are the instrument settings controlled by the operator. At an extruder temperature setting of 80° C., the infrared thermometer yielded a temperature value of about 63° C. This indicates that although the controller set temperature was 80° C., the melted extrudate inside the extruder barrel was exposed to a lower temperature in the extruder apparatus used in these runs.

As expected, the temperature measurement on the barrel surface was lower than the temperature setting of the extruder. During the heating process, the hopper opening was closed with a steel sheet to prevent heat loss. Next, PCL pellets were equilibrated to room temperature (r.t.), and weighed in three samples. The sample boats contained 7 g, 2 g and 2 g respectively.

1.2.3 Extrusion

After 1 hour, temperatures were measured at four different sections of the equipment—instrument setting indication, screw beginning, die opening and barrel surface. In making the fibers of this Experimental, the temperature measurement of the barrel surface was at least 62° C. prior to starting the extrusion process. After confirming that the barrel temperature was above 62° C., 7 g of PCL pellets were added to the hopper/screw beginning, and the 'extrude' button was switched on. After the elapse of 1 minute, an additional 2 g of pellets was introduced to the screw. After the elapse of another minute, the last 2 g of pellets was introduced to the screw. It was ensured that no PCL pellets were sitting on the sides of the hopper walls. After a total amount of 9 g was added to the screw, the hot-melt extrudate appeared at the die opening. From the beginning of the extrusion until the very end of the process, the average time to produce one batch of Efibers was approximately 3 hrs. The end point of the process was deemed as the point where the Efiber visibly thinned out. When this was observed, the extrusion process was stopped by switching the extruder off.

Approximately 1.5 meters was cut off from each end of the extruded Efiber. The middle section termed as the Efiber obtained from the 'equilibrium region' was stored in an outer foil pouch with a desiccant pouch inside. Afterwards, the foil pouch was heat sealed using an impulse sealer for 1.2 sec, under a 275° C. sealing temperature, and was stored in a dry place. Afterwards, the extruder was cleaned following the same protocol used for cleaning the extruder before experimentation. The above described Efiber manufacturing process was conducted three times at 80° C. to produce run ID numbers; 80C-2, 80C-3 and 80C-4. Efibers were each termed after their run ID number.

1.2.4 Speed of Efiber Extrusion

A hanging bar allowed the Efiber to free fall without touching the die opening area. If no such support was given to the Efiber, it coiled around the hot surface, which re-melted the extruded fiber.

To prepare the apparatus for Efiber collection, as well as data collection, the extruder die opening was brought close to the edge of a table. The Efiber extended over the hanging bar and was allowed to free fall and spool into a polypropylene bucket on the floor.

The Efiber was translucent as it exited the die opening. As it reached about 2 cm away from the die opening, the Efiber cooled down and turned opaque in appearance. To estimate the extrusion speed, the opaque region of the Efiber was visibly marked and the mark was timed over travel of a known distance (10 cm). This process was continued to obtain seven duration measurements. The extrusion speed was taken as the distance traveled by the mark divided by the time elapsed for the travel of the distance.

1.2.5 Diameter Measurements and Imaging

Images of both microfibers (Efiber and Sfiber) were obtained under Bright Field microscopy on an Olympus BX41, Clear Image Service Co., NH. SPOT software 5.0 was used to capture and analyze images. These images were used to determine the fiber diameters in the preliminary studies. For the remainder of experimentation conducted on groups 80C-2, 80C-3 and 80C-4, a micrometer was used to measure diameters of Efibers and Sfibers. Polarized Optical Microscopy was used to obtain images of the Efiber and Sfiber interiors.

1.2.6 Cold-stretching Efibers to Manufacture Sfibers

In order to manufacture the final Sfiber materials with reproducible results, the Instron tensile testing machine, and the ADMET horn grips were used for the entire study. Note the difference in the terminology in the distance between jaws (JD), and gauge length (GL). The term JD is explicitly used in Sfiber manufacturing, while the term GL is used in tensile testing.

In order to obtain the highest stretch %, a GL of 100 mm was used. In order for the Efiber to extend through both grips, and be clamped well to ensure no slippage, a minimum Efiber length of 145 mm was measured. A pull rate of 100 mm/min was used to stretch the Efibers. This was a moderate strain rate selected to allow the polymer molecules to align, relax and stabilize, while allowing the molecules to retain their initial molecular alignment. The stretching was discontinued when the upper ADMET grip reached the upper limit of the Instron Load Frame. This limitation was approx. 800 mm. When the instrument was zeroed at a GL of 100 mm, the starting extension value (Estart) was 0 mm, and the final extension value was $\varepsilon_{end}$.

$$\% \text{ stretch} = \frac{\varepsilon \cdot \text{end (mm)} - \varepsilon \cdot \text{start (mm)}}{GL \text{ (mm)}} \times 100 \qquad \text{Eqn. 3}$$

*Note: 15 mm JD=100 mm GL 100 mm GL accounts for the measurement of length around the horns.
*Note: Testing showed that the Efiber break point (at its maximum load) was not attainable at this travel limit on the Instron. Hence the extension ($\varepsilon_{end}$) at the break point during cold stretching was not determined.

1.2.7 Determining the End Point for Cold-stretching

In order to determine the end point for cold-stretching Efibers, three stopping points in the load-displacement curve were tested. Efibers (n=3) were stretched up until approx. 1 mm past the inflection point, mid-way into the stress-hardening region, and at the travel limit of the Instron upper grip. The extension ($\varepsilon_{end}$) corresponding to these stop point limits were 535 mm, 635 mm, and 735 mm respectively (Table 1). After stretching, the Sfibers were coiled/spooled around centrifuge tubes as elaborated in section 1.2.8. However, since these were not sterilized, instead of Tyvek pouches, they were directly inserted in outer foil pouches with a desiccant pouch inside each foil pouch to prevent moisture absorption during storage. They were heat sealed at 235° C. for 2 seconds, and left overnight to allow for molecular relaxation at their freshly aligned macromolecular configurations. The next day, tensile testing was conducted on the Sfibers to determine which cold-stretching $\varepsilon_{end}$ resulted in the highest tensile strength.

TABLE 1

Efiber % stretching achieved at three different stop points in the load-displacement curve.

|  | Level 1 | Level 2 | Level 3 |
| --- | --- | --- | --- |
| GL (mm) | 100 | 100 | 100 |
| $\varepsilon_{end}$ (mm) | 535 | 635 | 735 |
| % Stretching | 435.0% | 535.0% | 635.0% |

Note:
See section 2.2.6 for the selection of optimal Efiber % stretching parameters via tensile testing results of the Sfiber.

1.2.8 Packaging Sfibers for Sterilization in Preparation for the In Vitro Mechanical Strength Degradation Study The Sfibers were sterilized prior to the in vitro mechanical strength degradation study. The microorganism inactivation level of Ethylene oxide (EO) is categorized as high, and it penetrates all porous materials, some plastic materials and films. EO kills all known microorganisms such as mycobacteria, vegetative bacteria, bacterial spores, non-enveloped and enveloped viruses, prions, and fungi (including yeasts and molds). Since EO sterilization serves all the sterilization purposes required in this study, this technique was used to sterilize the Sfibers.

After manufacturing Sfibers, each Sfiber was carefully coiled around a 15 mL centrifuge tube, to provide the Sfiber structural support. This tube was then placed inside a larger (50 mL) centrifuge tube. The cap of the larger tube was left open so that EO was able to penetrate into the Sfiber samples. This assembly was carefully placed in a Tyvek pouch, and heat-sealed at 235° C. for 2 seconds near the cap region of the larger tube to prevent tube rotation inside the pouch. These precautions were taken in order to minimalize the possibility of the Sfiber being damaged or bent during transportation and handling. All 49 pouches (for the in vitro degradation study) were sent to an ethylene oxide gas (EO) sterilization cycle. After sterilization, the unopened Tyvek pouches were inserted in foil pouches with one desiccant pouch. Samples intended as controls were not subjected to sterilization. See section 1.2.11 for the methods carried out for tensile testing.

1.2.9 Stratification of Sfibers for the In Vitro Study

In order to accomplish inter-lot variability of Sfiber specimens, stratified randomization was conducted. After EO sterilization, Sfiber samples were placed in three separate boxes corresponding to their Efiber group ID numbers (80C-2, 80C-3, 80C-4). This is referred to as dividing the samples into strata. Six other empty boxes titled 2 wk, 3 m, 6 m, 9 m, and 12 m were prepared. These titles corresponded to each time point of the in vitro mechanical strength degradation DOE. Then onwards, the operator (without looking inside) randomly picked a total of seven samples from each box, and placed in the box allocated for '2 wk'. The same method was repeated for each time pt. In the same manner, another set of seven random samples were selected for the EO vs. Controls study.

1.2.10 In Vitro Mechanical Strength Degradation Study

In order to determine the mechanical strength degradation of Sfibers over a span of 1 year, randomized sterilized Sfiber specimens manufactured as described above were incubated as per ASTM 1635 in excess 0.01 M phosphate buffered saline (PBS); 7.4 pH at 37° C. The incubation process was conducted using aseptic technique in a laminar flow hood. In order to prevent any unknown interactions of the Sfiber and an antimicrobial reagent, no reagents were added to the solution. Seven samples per each time point were fully immersed in one bottle. A total of six separate autoclaved bottles were utilized for the entire study. ASTM 1635 specifies a minimum of six samples per time point for mechanical testing studies. However, in order to decrease standard error, increase precision, as well as leaving freedom for unforeseen experimental errors, 7 samples were used. In order to address inter-lot variability for future process validation purposes, Sfibers manufactured from three different groups of Efibers were used. This meets the minimum ASTM 1635 requirement for addressing inter-lot variability.

pH of the 0.1 M phosphate buffered saline (PBS) medium, was maintained at 7.4±0.2. Whenever the PBS medium was changed, the pH of the outgoing PBS (old), and pH of the incoming (new) PBS was recorded on the 'pH recording sheet'. The outgoing pH was recorded for each bottle. The incoming pH (new) is simply one value, as the incoming PBS for all bottles were used from one PBS stock solution. The pH meter precision requirements as per ASTM 1635-04a should be 0.02 or better, and the pH meter used for the study (ETI: 11010) had a High Accuracy Limit (HAL) of ±0.01 pH, which is adequate to meet the ASTM 1635-04a precision requirement. Before measuring pH of PBS, the pH meter was calibrated using pH=7.0, and pH=9.21 standard buffer solutions. Frequency of PBS medium replacement was once per/month (±3-5 days)..The removal of old PBS was performed via means of decantation aided by an autoclaved Teflon mesh as needed. The addition of new PBS was performed carefully in a laminar flow hood. In order to prevent contamination, all handling of bottles during PBS replacement was conducted under aseptic technique. The incubator temperature was maintained at 37±2° C., and the incubator stage was shaken at a 60 to 70 RPM. The t=0 data collected on day 1 was subjected to 1 hr of incubation in 0.01 M PBS at 37±0.1° C.

1.2.11 Tensile Strength Testing and Mechanical Strength Properties

Tensile testing of the final Sfiber prototypes was conducted according to ASTM D2256-10; Standard Test Method for Tensile Properties of Yarns by the Single-Strand Method. The test samples were loaded to 0.1 N at a pull rate of 50 mm/min to remove the toeing region. During the pre-load period, no data were recorded. Data outliers were identified in the tensile testing when a kink or a bump was felt when the thumb and index fingers were run along the Sfiber surface. The outlier data were excluded from calculations.

The % strain was calculated as per eqn. 4, where GL was 250 mm. The $\varepsilon_{end}$ value is the extension at the load at failure. $\varepsilon_{beginning}$ is the starting strain value soon after the preload is completed. This is the point where the tensile test started, and data collection began by the Bluehill° software utilized. The variables computed and reported are the tensile stress calculated by eqn. 5, strain calculated by eqn. 4, and the Elastic Modulus calculated by eqn. 6. The Elastic Modulus is also termed as the tensile modulus, and is an indication of how stiff a material is. Stiffness is the reluctance to bending. A higher Elastic Modulus corresponds to a stiffer material.

$$\text{strain}(\varepsilon, \%) = \frac{\varepsilon \cdot \text{end (mm)} - \varepsilon \cdot \text{beginning (mm)}}{GL \text{ (mm)}} \quad \text{Eqn. 4}$$

$$\text{stress} = \frac{\text{Load at failure }(N)}{\text{cross sectional area }(m^2)} \quad \text{Eqn. 5}$$

$$\text{Elastic Modulus} = \frac{\text{Stress (MPa)}}{\text{Strain}(\varepsilon, \%)} \quad \text{Eqn. 6}$$

2. Results and Discussion

2.2.1 The Effect of Extrusion Temperature on the Sfiber Diameter

To study whether the temperature of the extrusion process had an effect on the Sfiber diameter, optical microscopy was used. As mentioned above, 80° C., 90° C. and 100° C. extrusion temperature settings on the extruder were successful in yielding consistent extrudate throughput. Albeit making triplicate diameter measurements of seven separate Sfibers for each extrusion temperature, we are unable to make complete statistical attributions because we did not manufacture triplicate Efiber groups at each extrusion temperature (only for 80° C.). Also, the Sfibers used in the testing for this section 2.2.1 were not stretched to 635% (into stress hardening) as for Sfibers tested in other sections of this Experimental, but were only stretched until opaque regions of the Efiber dissipated completely by visual inspection, which was before stress hardening had occurred. Nonetheless, a recognizable trend was noted toward decreasing fiber diameter with increasing extrusion temperature.

TABLE 2

Diameters of Sfibers manufactured from Efibers extruded at three temperatures.

| Temperature of extrusion (° C.) | Avg. diameter (pm) | SD (pm) | % CV | sample size |
|---|---|---|---|---|
| 80 | 406.97 | 15.78 | 3.88 | 7 |
| 90 | 372.70 | 27.50 | 7.38 | 14 |
| 100 | 296.72 | 13.60 | 4.58 | 7 |

Note:
90° C. data were pooled from two extrusion process runs which followed the same steps.

2.2.2 Surface Properties of Fibers

Figure 3A:
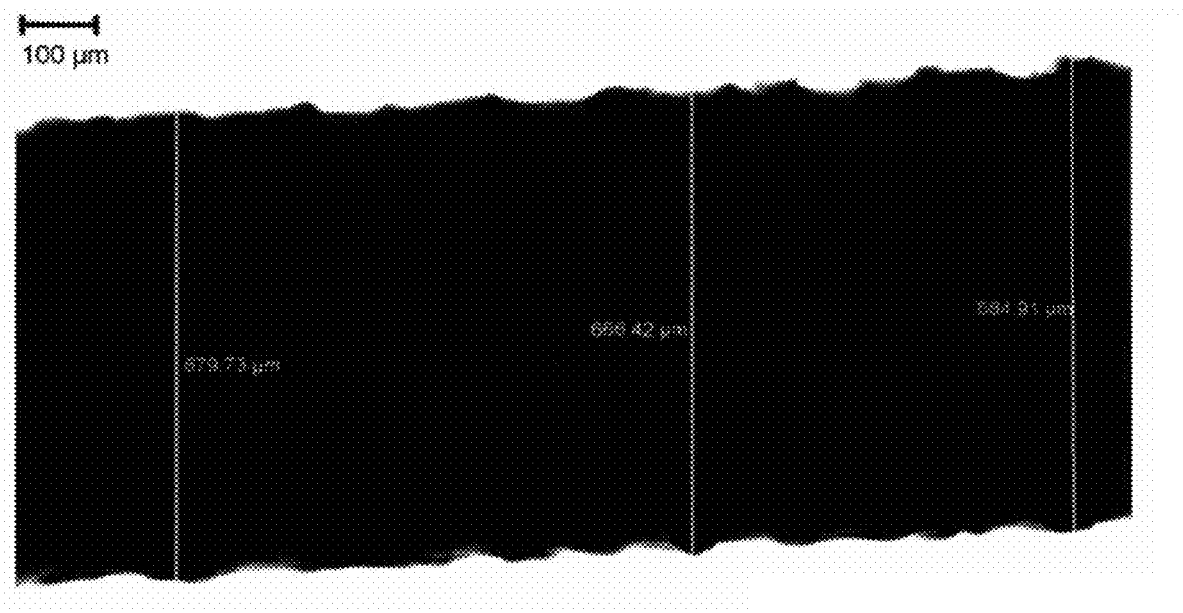
FIGS. 3a and 3b are images that show an Efiber segment obtained from before the arrival of the equilibrium region and from the equilibrium region, respectively, as described further in the Experimental set forth below.
Figure 3B:
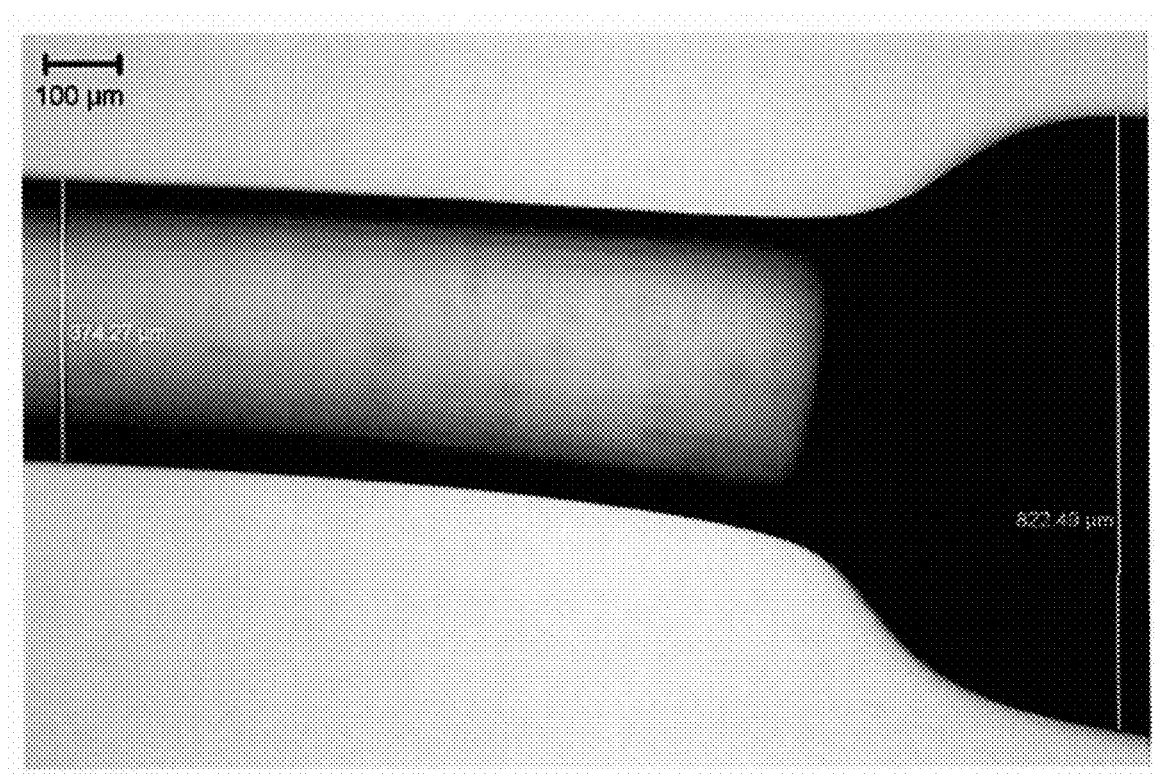

An Efiber segment obtained from before the arrival of the equilibrium region shows clear ruggedness in the optical microscope images (FIG. 3a). These surface properties propagate to the Sfiber as well. Efibers obtained from the equilibrium region do not exhibit such rugged properties, and their representative Sfibers appear very smooth (FIG. 3b).

2.2.3 Efiber Speed at 80° C.

We determined the Efiber output speed at the very beginning of the extrusion process and at the beginning of the 'equilibrium region'. The equilibrium region is where we considered that the extruding speed has reached an acceptable consistency, and where the Efiber diameter was uniform. Efibers from this region were selected to manufacture Sfibers. Results show that at the very beginning of the process, the Efiber is produced at a faster rate. After about 15 mins of the batch process, the speed eventually stabilizes, until it visually slows down towards the very end of the process (as the hot extrudate begins to deplete).

2.2.4 Effect of Cold-stretching on the Physical Nature

Figure 4:
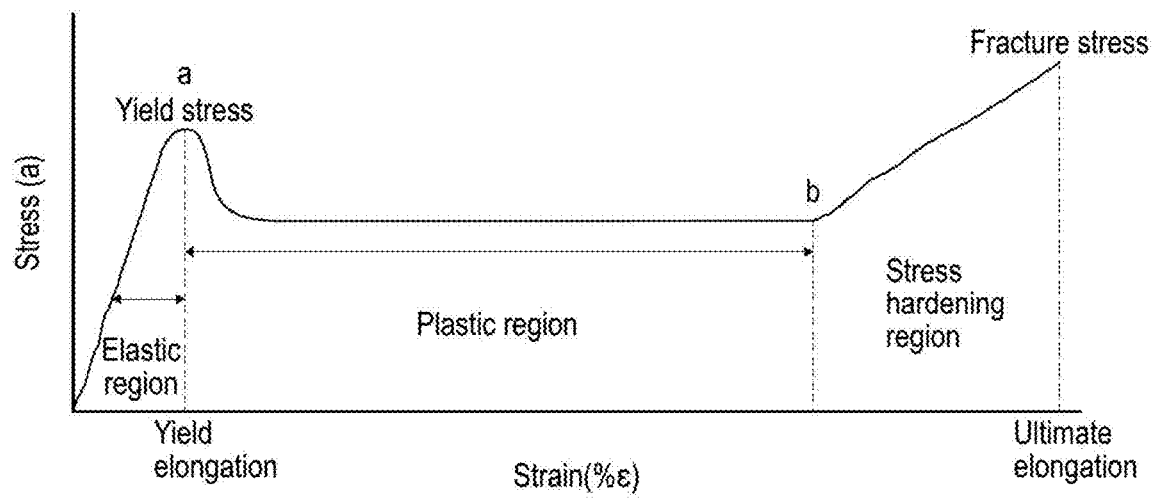
FIGS. 4 to 11 are graphs, charts or digital images generated as a part of, and are further described in, the Experimental set forth below.
Figure 5A:
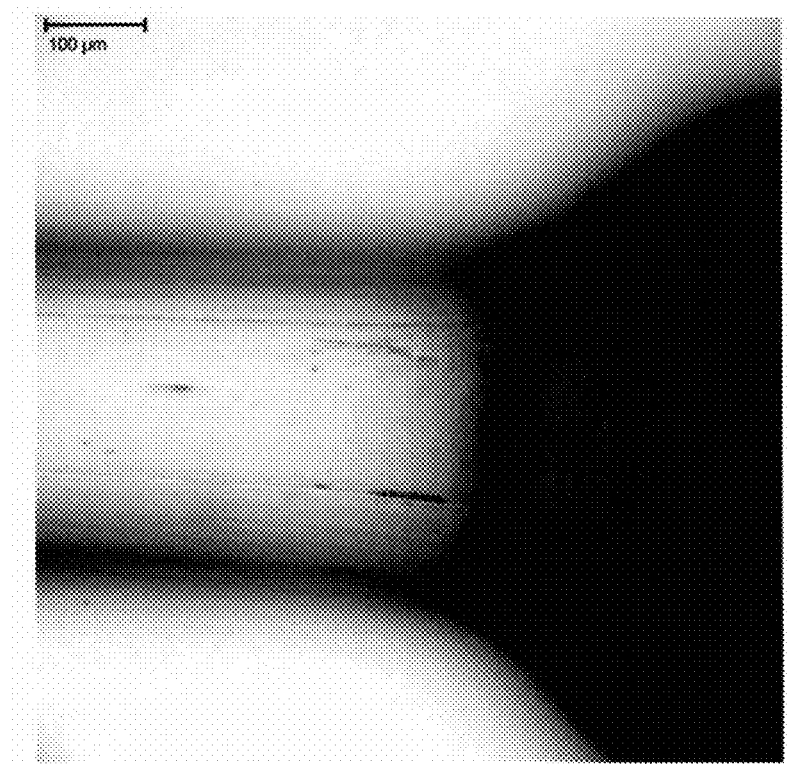
Figure 5B:
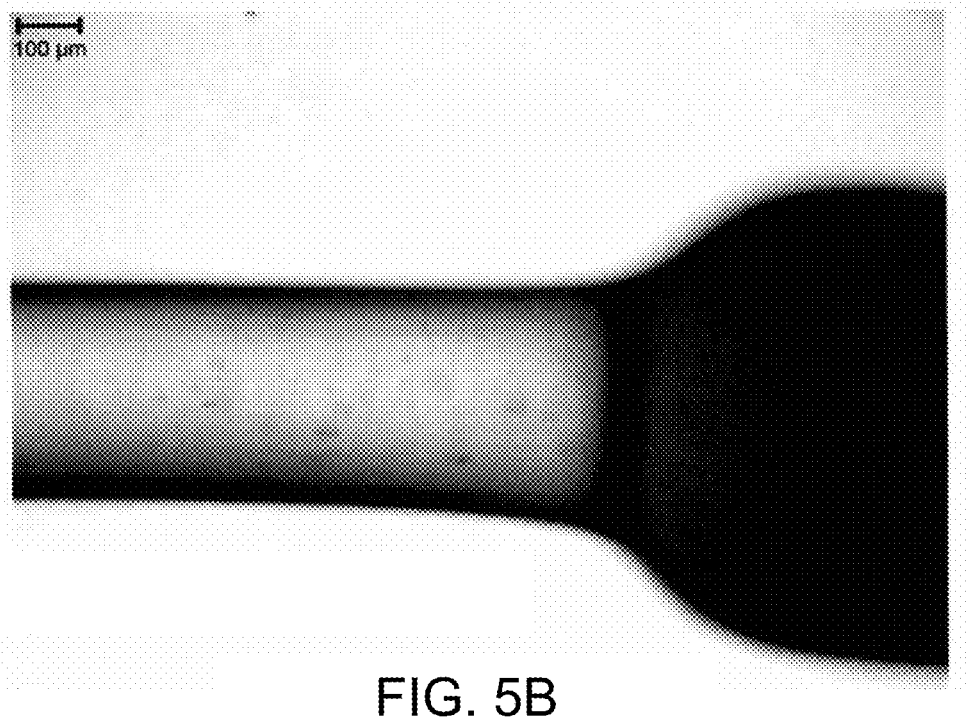
Figure 5C:
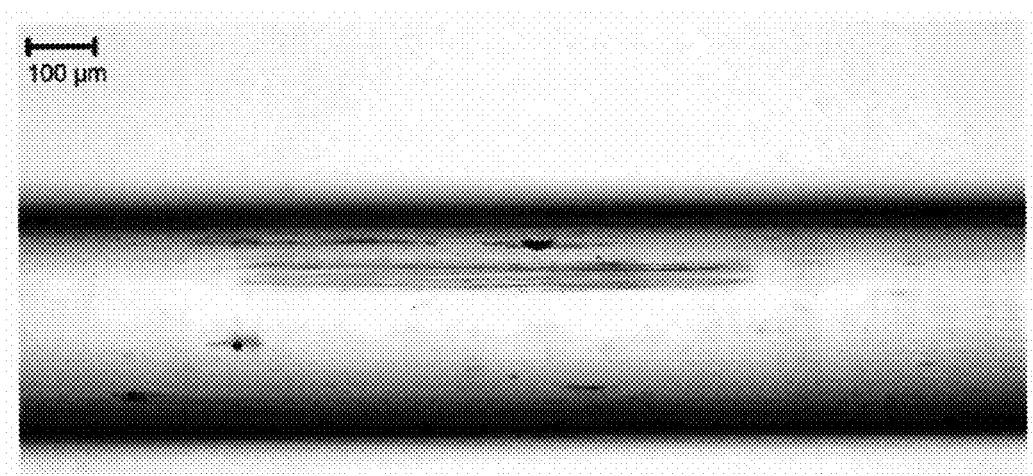

PCL is a semi-crystalline polymer containing both crystalline and amorphous regions. The crystalline regions could be referred to as the hard phases which provide dimensional stability of molecules through orderly alignments of molecules. The amorphous regions are randomly packed, and are responsible for the elastomeric properties of the polymer. During the cold stretching process, the applied strains straighten the tangled amorphous regions, and align the crystalline regions into a linear form. Once the yield stress is exceeded the polymer deforms plastically (Fig. 4). The next phase which is the plastic deformation is the result of chains sliding, stretching, rotating, and disentangling under load. This causes permanent deformation. As seen in Fig. 4, there is a drop in stress beyond the yield point. This is because the initially tangled and intertwined amorphous chains become untangled. The chains then begin to straighten. Once the chains are straightened, after stage 3, the crystalline blocks as well as the chains continue to align in the tensile-axis, and enter the stress-hardening region. We believe that this stress hardening contributes to enhanced mechanical strength properties, combined with other beneficial mechanical properties, for the Sfibers. The fibrous appearance of the Sfiber interior sections observed through light microscopy and Polarized Optical Microscopy (POM) provides support for this (see FIGs. 5a, 5b, and 5c).

2.2.5 Efiber and Sfiber Diameters at 80° C.

Figure 6:
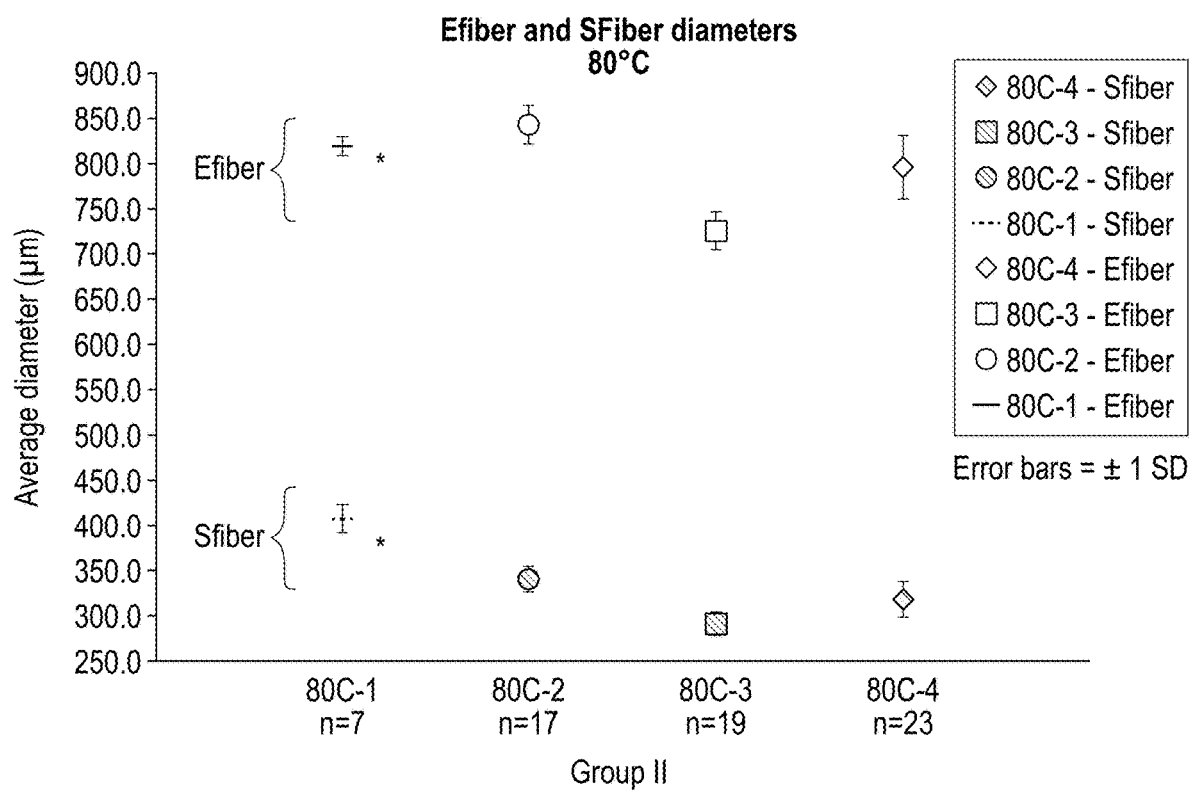

The average diameter reduction due to the cold-stretching process from groups 80C-2, 80C-3 and 80C-4 was 472.5 pm. It should be noted that group 80C-1 Sfiber results were obtained from stretching the Efibers up until visual dissipation of opaque regions. It was decided that visual observation of opaque region dissipation did not completely remove the plastic phase of Efibers. i.e., the cold-stretching process was not conducted as extensively as desired. Therefore, although 800-1 S fiber results were included in the graph in FIG. 6, the diameter measurements of 800-1 were excluded from the above reported diameter average. The other three groups were stretched up until the finalized process parameter, $\varepsilon_{end}$ (refer to section 1.2.7).

2.2.6 The Effect of % Stretching on the Tensile Strength of Sfiber

Figure 7A:
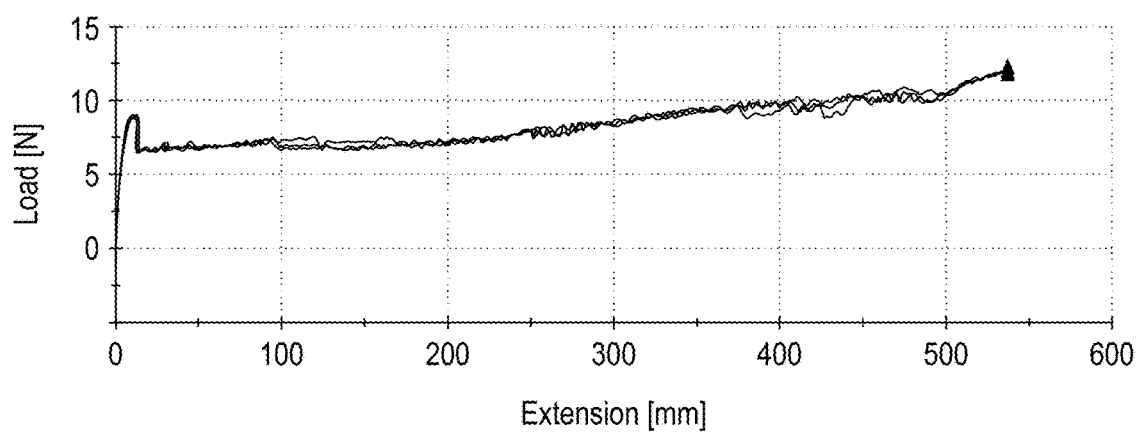
Figure 7B:
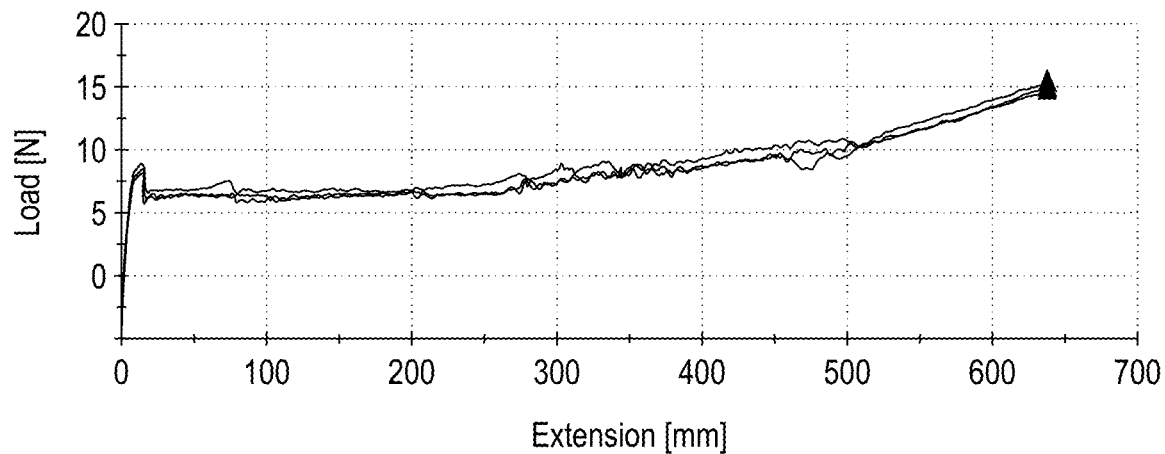
Figure 7C:
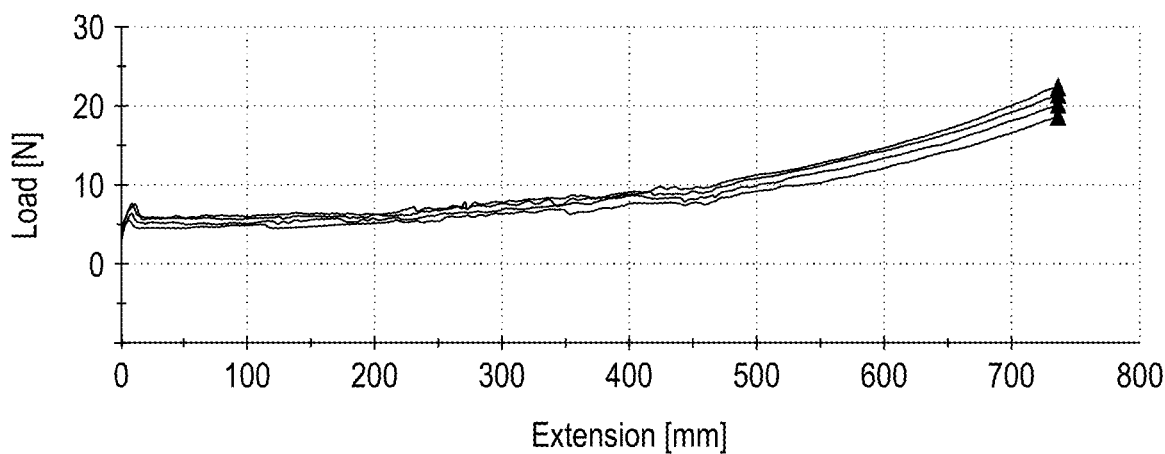

The tensile strength properties of the Sfibers manufactured at three different levels of the process parameter ($\varepsilon_{end}$) allowed us to determine which % stretching yielded the highest tensile stress, highest Elastic Modulus and the lowest % strain, given the instrument limitations. FIGS. 7a, 7b and 7c show the Efiber stretching profiles at each end level of stretching. The inflection point of the Efiber (where the Efiber plastic deformation region ends and the stress-hardening region begins) was between 460-500 mm in the work conducted.

The tensile strength results from the stretch end level 3 (FIG. 7c) resulted in the lowest % strain (53%), highest stress (551.29 MPa) and the highest Elastic Modulus (1039.66 MPa) for the produced fiber. These results demonstrated the benefits of a process parameter for $\varepsilon_{end}$ for this cold-stretching process at stop point level 3, which was at 735 mm (Table 3).

TABLE 3

Effect of the extent of stretch in thes Sfiber mechanical strength properties.

| Level | % Stretch | Avg. Strain % | Stress (MPa) | Modulus (MPa) |
|---|---|---|---|---|
| 1 | 435.0% | 94% | 537.45 | 570.72 |
| 2 | 535.0% | 70% | 525.05 | 744.68 |
| 3 | 635.0% | 53% | 551.29 | 1039.66 |

Note:
n = 3 for level 1 & 2.
n = 4 for level 3.

Figure 8:
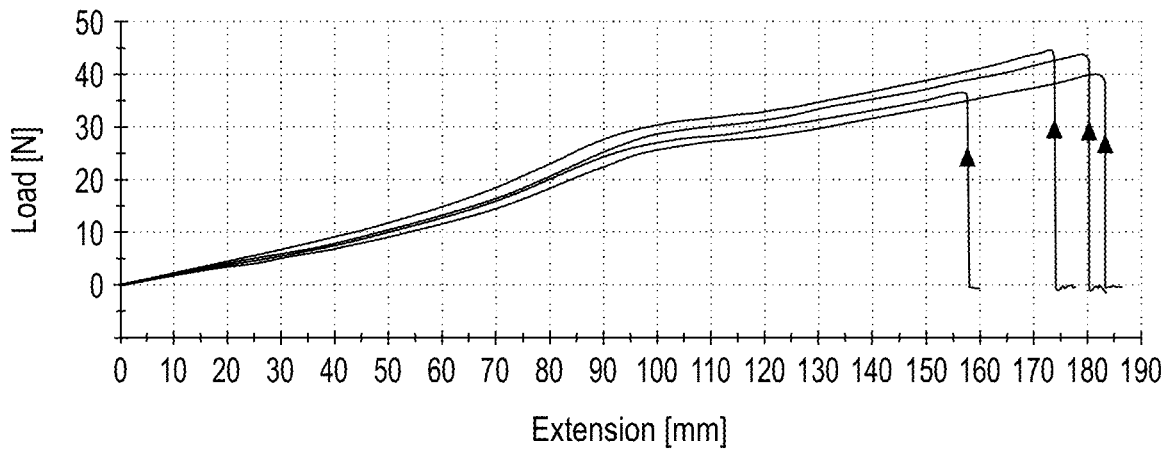

At this stop point level 3, we expected the Sfiber to retain its initial molecular alignment and structure once it was passed well beyond the stress-hardening region. Although at macro-molecular level, there may have been some miniscule molecular relaxation, it was not expected to occur at mm levels. Aligning well with this expectation, the tensile strength profiles of the final Sfibers did not show any initial plateauing corresponding to plastic deformation (FIG. 8).

2.2.7 Effect of EO Sterilization on the Elastic Modulus of the Sfibers

The absolute difference values between the control group and the EO sterilization group were compared, where n=7/group. Both the control and EO sterilized groups contained randomized Sfibers from 80C-2, 80C-3, 80C-4, and they were tested at dry conditions. Absolute difference calculations show that after EO sterilization, the tensile strength of the Sfibers reduced by 30.5 MPa, the % strain increased by 7%, and the Young's Modulus decreased by 186.2 MPa. Albeit the small sample size per group (n=7), an unpaired Student's t-test was conducted to determine if this was a significant difference. The groups were not paired as each Sfiber used for the control group and EO sterilized group were derived from separate Efibers. Therefore, the control and the EO sterilized groups were treated as two different populations. The Student's t-test yielded a two-tailed p-value of 0.0086 and 0.0004 (p<0.05), for the Young's Modulus and % strain respectively, indicating that there is a significant difference in these two parameters after the specimen samples were EO sterilized. However, with a p-value of 0.3590, the tensile stress appears to be unaffected by EO sterilization. The contributing factor to the decreased Elastic Modulus is perhaps the % strain. The absolute difference between the tensile stress was only 30.5 MPa while the % strain increased from 7% in the EO group. This in turn led to a reduction of 186.5 MPa in the Elastic Modulus.

TABLE 4

Results of the Controls and EO sterilization
study groups (n = 7/study group)

|  | Tensile Stress ($\sigma$, MPa) | Strain ($\varepsilon$, %) | Elastic Modulus (MPa) |
| --- | --- | --- | --- |
| Controls | | | |
| Avg. | 494.1 | 48.5% | 1020.5 |
| SD | 61.0 | 1.9% | 133.9 |
| % CV | 12.3% | 3.9% | 13.1% |
| EO sterilized | | | |
| Avg. | 463.6 | 55.5% | 834.0 |
| SD | 58.6 | 3.3% | 82.5 |
| % CV | 12.6% | 5.9% | 9.9% |

Note:
Sfibers were produced from 80C-2, 80C-3 and 80C-4 Efiber groups.

2.2.8 In Vitro Mechanical Strength Degradation Study, Rehydration Duration for $t_0$ Sfiber manufactured (stretched to level 3) from Efiber group 80C-4 were subjected to an internal study to determine if there was a difference among dry state (n=6), and phosphate buffered saline immersion periods of 10 min (n=5) and 60 min (n=6). The average Sfiber diameter of 80C-4 was 318.5 pm. The calculated average cross sectional area of the Sfibers was $7.97 \times 10^{-8}$ m².

In order to address some potential in vivo and clinical applications of the developed novel fiber, the t=0 results were obtained after rehydration. In order to test if the water absorption of the thin Sfiber arrives at a steady state by clinically relevant durations, 60 min was chosen as the t=0 results to be compared with other time point results in the in vitro degradation study. Mechanical strength properties of Sfiber in dry state, and after 10 min immersion and 60 min immersion under physiologic conditions (0.01 M PBS; pH 7.4±0.2; 37±0.02° C.) are shown in Table 5.

TABLE 5

Differences in mechanical strength properties at t = 0,
under three different conditions;
dry condition, after 10 min, and 60 min PBS immersion.

|  | Tensile Stress ($\sigma$, MPa) | Strain ($\varepsilon$, %) | Elastic Modulus (MPa) |
| --- | --- | --- | --- |
| Dry condition | | | |
| Average | 633.4 | 53.1% | 1192.2 |
| SD | 63.7 | 4.8% | 29.4 |
| % CV | 10.1% | 9.1% | 2.5% |
| 10 min immersion | | | |
| Average | 595.92 | 52.5% | 1133.0 |
| SD | 96.48 | 7.9% | 35.8 |
| % CV | 16.2% | 15.0% | 3.2% |
| 60 min immersion | | | |
| Average | 599.1 | 55.2% | 1085.3 |
| SD | 61.3 | 4.1% | 74.6 |
| % CV | 10.2% | 7.4% | 6.9% |

Note:
Sfibers were not EO sterilized.
Dry condition and 60 min; n = 6 Sfibers. 10 min; n = 5 Sfibers.
Sfibers were all produced from 80C-4 Efiber group.
GL = 25 cm (in accordance with ASTM)

An absolute reduction of 47.7 MPa in the Elastic Modulus was observed between 60 min and 10 min rehydration periods. The largest contributing factor to this reduction in the Modulus may be the increase in % strain in the 60 min group. Although there was an increase of tensile strength by 3.2 MPa, there was also an increase of % strain by 2.7%, which resulted in a lower Elastic Modulus for 60 min. The standard deviation of tensile stress and % strain in the 10 min group appears higher as compared to the dry condition and 60 min group. The reason for the increase in the variance of sample mean is suspected to be due to transient state of water diffusion into the microfiber. Water diffusion into these fibers is very fast compared to water-mediated hydrolysis. It is possible that water is perhaps only uniformly distributed within the polymer surface or the near-surface layer after 10 min. Therefore, we chose the 60 min rehydration period to continue tensile testing the EO sterilized Sfibers reserved to conduct to data.

2.2.9 In Vitro Mechanical Strength Degradation Study, $t_0$ and $t_1$

Figure 9A:
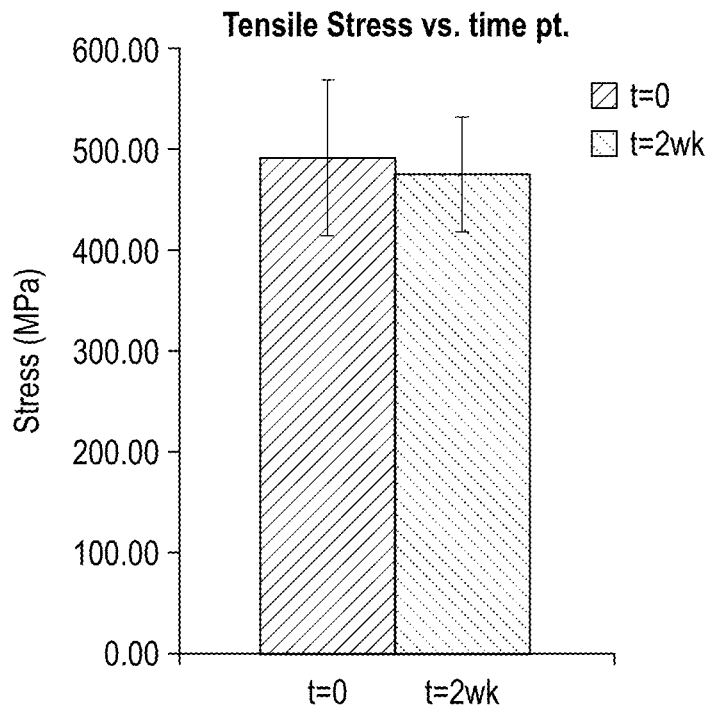
Figure 9B:
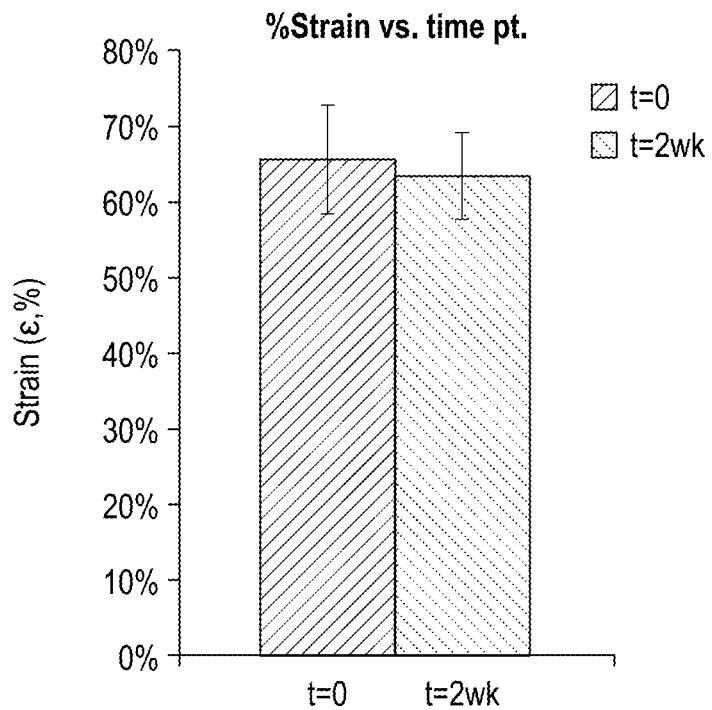
Figure 9C:
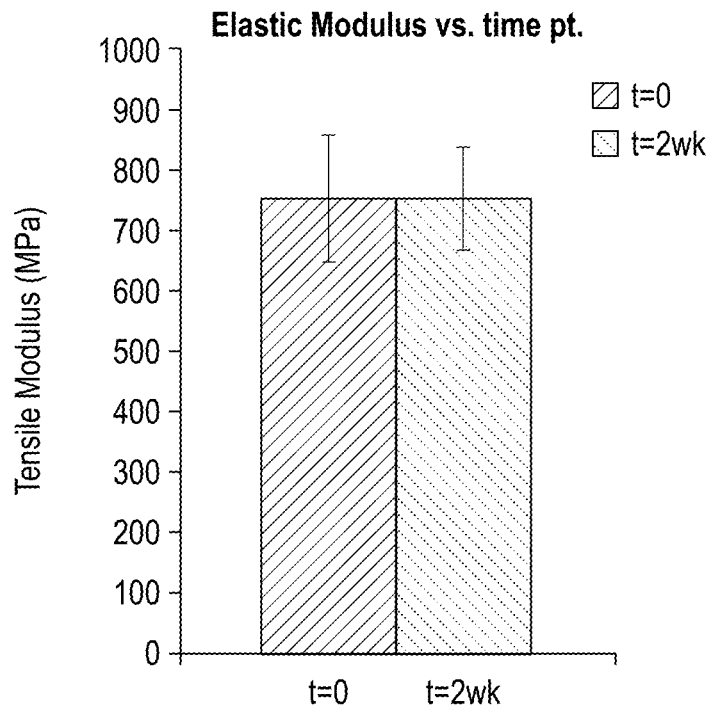

After choosing that to testing would be conducted after 60 min rehydration, the EO sterilized, stratified Sfiber samples were tested after incubation for 60 min under physiologic conditions (immersion in phosphate buffered 0.9% saline, pH 7.4, at 37° C. with 60-70 rpm shaking). FIGS. 9a, 9b and 9c illustrate that after two weeks of incubation, mechanical properties of the Sfibers were practically unaffected. In order to determine where there was a statistically significant difference between the three mechanical strength properties, an unpaired Student's t-test was conducted between the two time points. The results indicated no statistically significant difference between the tensile stress (p=0.649), % strain (p=0.536), and the Elastic Modulus (p=0.991).

Figure 10A:
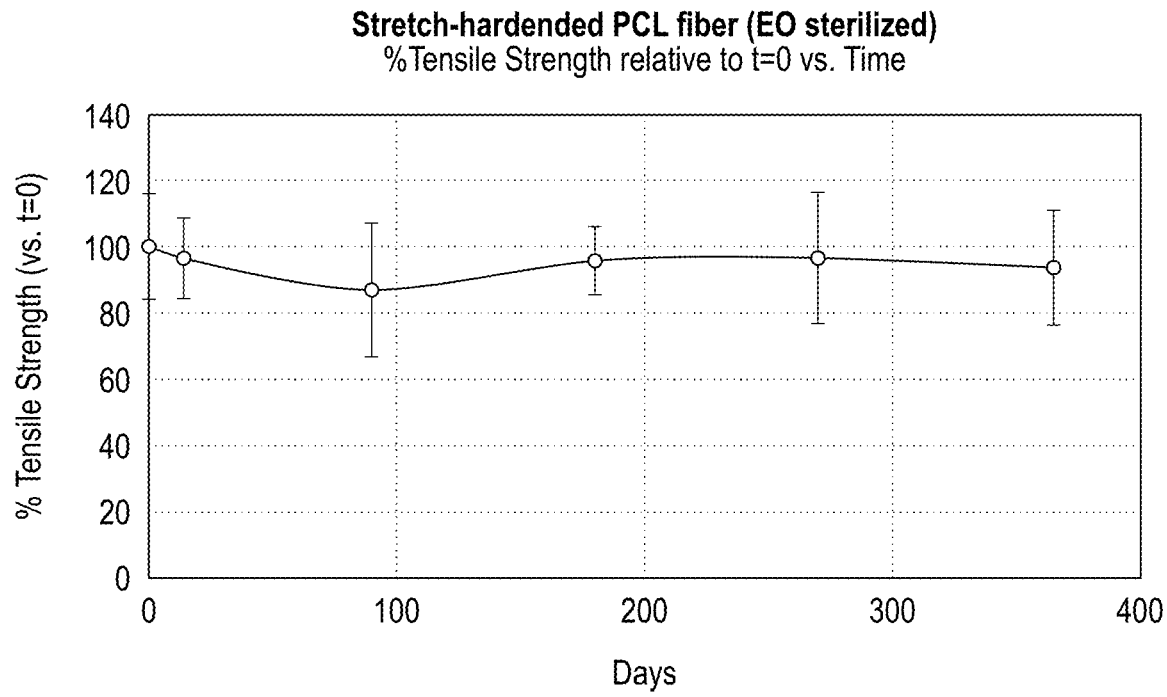
Figure 10B:
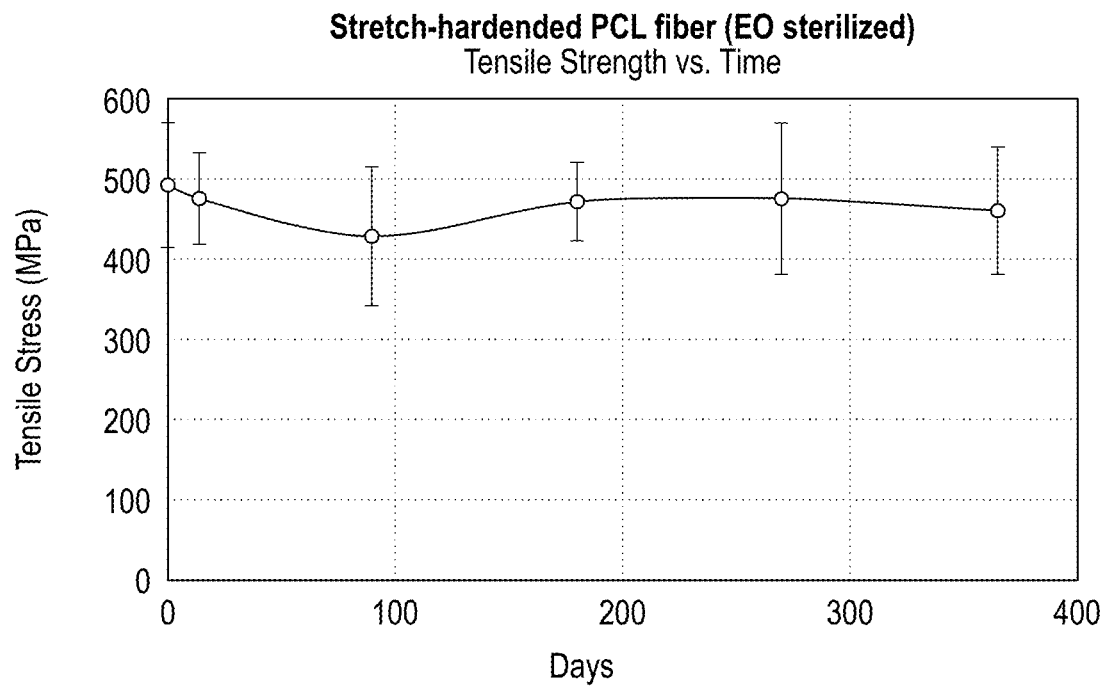
Figure 10C:
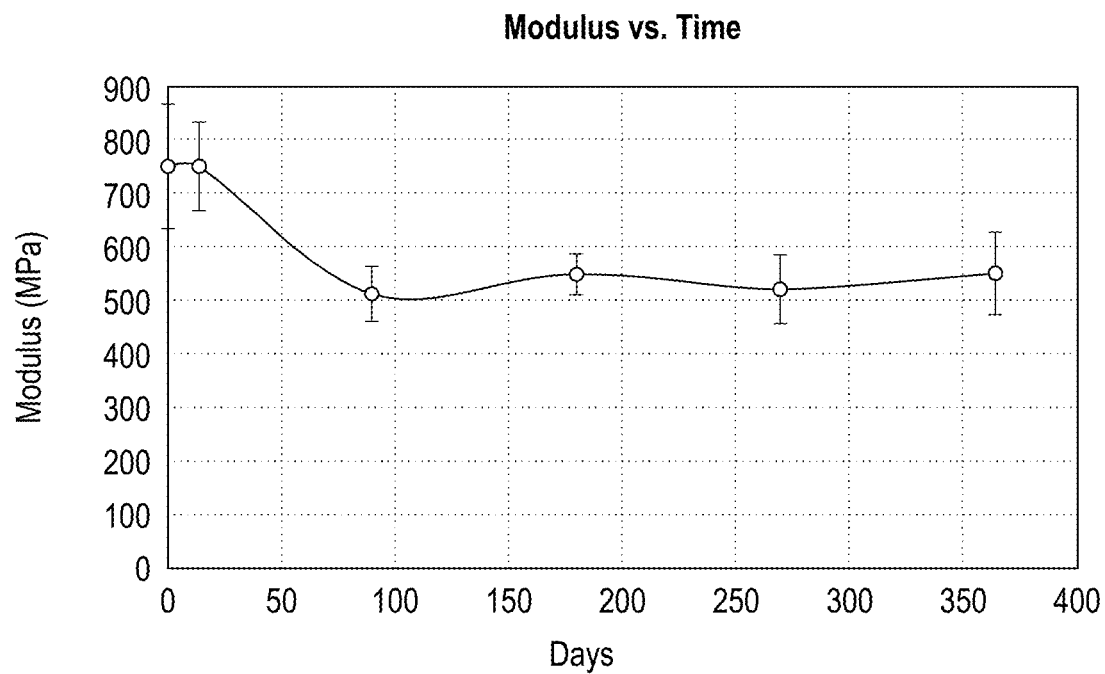
Figure 10D:
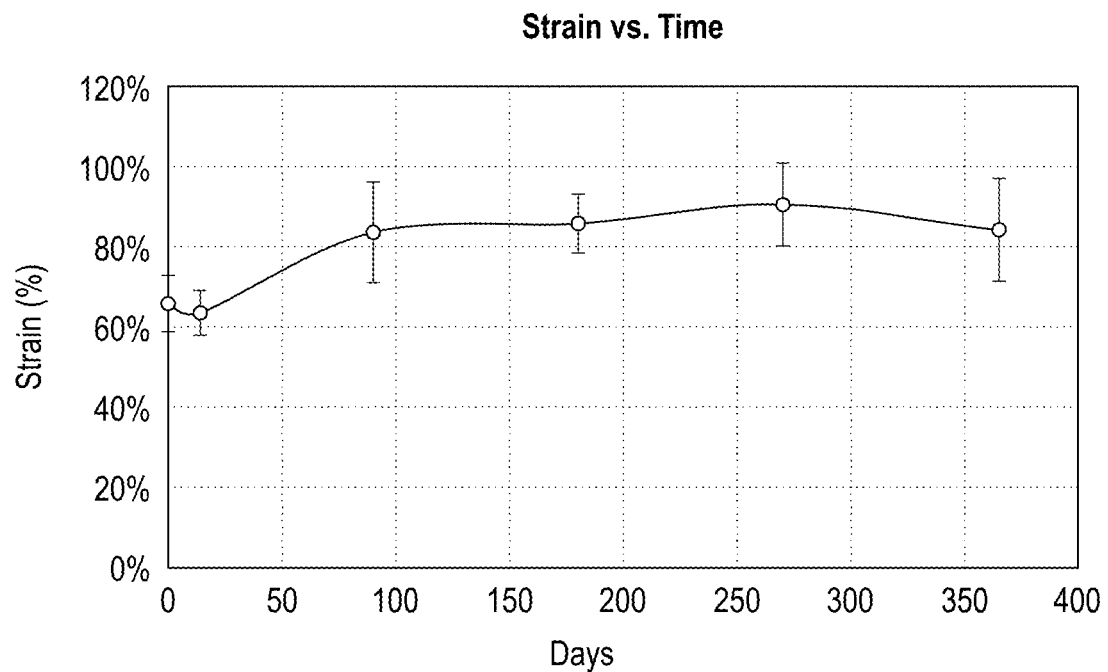

The degradation study times were extended with solution changes every month and monitoring the pH of the solution at change. 7 specimens were selected at each of the following time points: 2 weeks, 3 months, 6 months, 9 months and 12 months. The diameter of the fiber specimens was measured at each extreme end and averaged. The mechanical properties of the fiber specimens are shown in FIGS. 10a, 10b, 10c, and 10d. As shown in FIGS. 10a and 10b, the tensile strength of the fibers remained essentially unchanged or trended to only slightly decreased (~10%) relative to to over the 12 month study. As shown in FIGS. 10c and 10d, the tensile strain increased from about 65% to 80-85% and the elastic modulus decreased from about 750 MPA to about 500-550 MPa over the course of the 12 month study.

Figure 11:
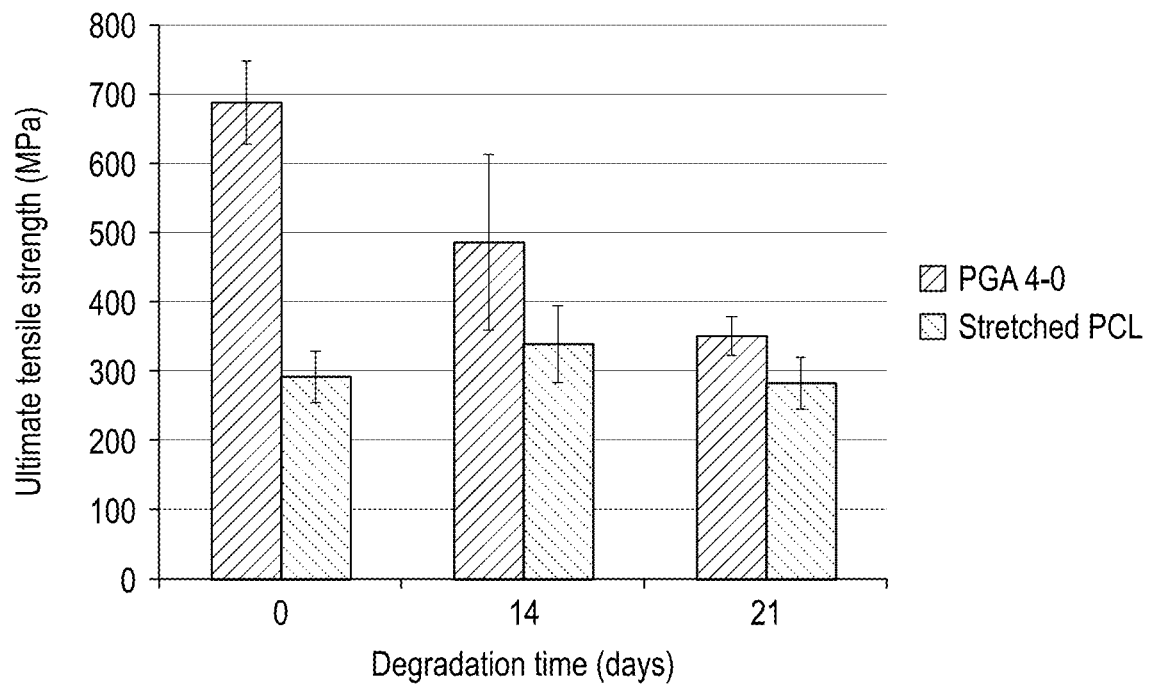

In addition to the specimens tested at these time points, specimens of the Sfibers and of similarly processed 4-0 polyglycolic acid (PGA) suture were tested for ultimate tensile strength after 21 days of the incubation. The results are provided in FIG. 11, and show that the PGA suture material exhibited about a 50% decrease in ultimate tensile strength over the 21 days, whereas the Sfibers exhibited essentially no change in ultimate tensile strength over this period.

CONCLUSIONS

At 80° C., the average diameter of the extruded polycaprolactone fibers was 789 pm. Due to cold-stretching, the average diameter of the microfiber reduced from an average of 789 pm to 317 pm. Light microscopy indicated rudimentary evidence for an increased degree of crystalline structure in the fiber interior.

There was a direct correlation between the extent of stretching during the cold-stretching process and the tensile strength of the resulting fiber. After cold-stretching extruded fibers to the maximum extent of stretching used here, the resulting novel fiber surprisingly yielded a tensile strength value of 551 MPa and an Elastic Modulus of 1039 MPa. The elasticity (% strain) of the novel material reduced to 53%. Ethylene Oxide (EO) sterilization decreased the tensile stress and the Elastic Modulus, and increased the % strain. The tensile strength of the novel material after 60 min of rehydration was 599 MPa, and the Elastic Modulus was 1085 MPa. After 2 weeks, there was no statistically significant difference between the tensile stress, % strain and the Elastic Modulus. The tensile strength of the novel material remains essentially the same or decreases only slightly after a year of agitated incubation in PBS at 37° C. while the tensile strain moderately increases and the elastic modulus moderately decreases.

The uses of the terms "a" and "an" and "the" and similar references herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the products or methods defined by the claims.

All references cited herein are indicative of the level of skill in the art and are hereby incorporated by reference in their entirety.

While embodiments of the disclosure have been illustrated and described in detail in the drawings and foregoing description, the same is to be considered as illustrative and not restrictive in character, it being understood that only some embodiments have been shown and described and that all changes and modifications that come within the spirit of the disclosures herein are desired to be protected. As examples, the following Listing of Certain Disclosed Embodiments provides an identification of some of the embodiments disclosed herein. It will be understood that this listing is non-limiting, and that individual features or combinations of features (e.g. 2, 3 or 4 features) as described in the Detailed Description above can be combined with the below-listed, enumerated Embodiments of the Listing of Certain Disclosed Embodiments to provide additional disclosed embodiments herein.

LISTING OF CERTAIN DISCLOSED EMBODIMENTS

Embodiment 1. A melt extruded, oriented polymeric material fiber, wherein the polymeric material is a homopolymer of caprolactone or a copolymer of at least 90% by weight of caprolactone and one or more additional monomers.

Embodiment 2. The melt extruded, oriented polymeric material fiber of Embodiment1, wherein the polymeric material has been stress hardened by stretching.

Embodiment 3. The melt extruded, oriented polymeric material fiber of Embodiment 1 or 2, wherein the polymeric material fiber has a tensile strength of about 450 MPa to about 650 MPa, and/or an elongation at break in the range of 45% to 65%, and/or an elastic modulus in the range of 750 MPa to 1200 MPa.

Embodiment 4. The melt extruded, oriented polymeric material fiber of any preceding Embodiment, wherein the polymeric material fiber has a tensile strength in the range of about 500 MPa to about 650 MPa.

Embodiment 5. The melt extruded, oriented polymeric material fiber of any preceding Embodiment, which has been prepared by a method comprising melt extruding the polymeric material to form an extrudate, allowing the extrudate dwell time to crystallize, and drawing the extrudate.

Embodiment 6. The melt extruded, oriented polymeric material fiber of any preceding Embodiment, wherein the polymeric material fiber has an average diameter in the range of about 0.01 to about 0.4 mm, preferably about 0.1 to 3 mm.

Embodiment 7. The melt extruded, oriented polymeric material fiber of any preceding Embodiment, wherein the polymeric material fiber has a crystallinity above 35%, and optionally in the range of 35% to 50%.

Embodiment 8. The melt extruded, oriented polymeric material fiber of any preceding Embodiment, wherein the homopolymer or the copolymer is a linear polymer.

Embodiment 9. The melt extruded, oriented polymeric material fiber of any preceding Embodiment, wherein the tensile strength of the fiber, as measured after immersion in phosphate buffered physiological saline for 60 minutes, decreases less than 20% after immersion in phosphate buffered physiological saline for 6 months.

Embodiment 10. The melt extruded, oriented polymeric material fiber of any preceding Embodiment, wherein the polymeric material fiber has an elongation at break in the range of 45% to 65%.

Embodiment 11. The melt extruded, oriented polymeric material fiber of any preceding Embodiment, wherein the polymeric material is a homopolymer of caprolactone.

Embodiment 12. The melt extruded, oriented polymeric material fiber of any one of Embodiments 1 to 10, wherein the polymeric material is a copolymer of at least 90% by weight of caprolactone and one or more additional monomers.

Embodiment 13. The melt extruded, oriented polymeric material fiber of any preceding Embodiment, wherein the number average molecular weight of the homopolymer or the copolymer is in the range of about 10000 to about 150000 kDa, preferably about 40000 to about 100000 kDa.

Embodiment 14. The melt extruded, oriented polymeric material fiber of any preceding Embodiment, which has been sterilized.

Embodiment 15. The melt extruded, oriented polymeric material fiber of Embodiment 14, which has been sterilized by exposure to ethylene oxide gas.

Embodiment 16. A medical device comprising one or more melt extruded, oriented polymeric fibers according to any one of Embodiments 1 to 15.

Embodiment 17. The medical device of Embodiment 16, wherein the device is a medical textile, tube, surgical mesh, hernia mesh, breast reconstruction mesh, mastopexy mesh, pericardial patch, anti-adhesion patch, cardiovascular patch, guided tissue regeneration patch, sling, monofilament suture, multifilament suture, ligament repair device, tendon repair device, meniscus repair device, cartilage repair device, nerve guide, stent, vascular graft, or dura repair device.

Embodiment 18. The medical device of Embodiment 16, wherein the device comprises a knitted mesh, woven mesh, or nonwoven mesh comprising one or more of the melt extruded, oriented polymeric fibers.

Embodiment 19. The medical device of Embodiment 18, wherein the knitted mesh, woven mesh, or nonwoven mesh has a density in the range of about 30 to about 100 g/m².

Embodiment 20. The medical device of Embodiment 18 or 19, wherein the knitted mesh, woven mesh, or nonwoven mesh has an average pore size in the range of about 0.25 square micrometers to about 2500 square micrometers.

Embodiment 21. The medical device of any one of Embodiments 18 to 20, wherein the knitted mesh, woven mesh, or nonwoven mesh has a tensile strength of greater than about 30 N/cm.

Embodiment 22. The medical device of any one of Embodiments 18 to 21, wherein the knitted mesh, woven mesh, or nonwoven mesh has a suture retention strength of greater than about 20 N.

Embodiment 23. The medical device of any one of Embodiments 18 to 22, wherein the knitted mesh, woven mesh, or nonwoven mesh has a ball burst strength of greater than about 50 N/cm.

Embodiment 24. The medical device of any one of Embodiments 18 to 23, wherein the knitted mesh, woven mesh or nonwoven mesh is constituted at least 50% by weight of said melt extruded, oriented polymeric material fibers.

Embodiment 25. The medical device of any one of Embodiments 18 to 24, wherein said melt extruded, oriented polymeric material fibers are the only fibers of the knitted mesh, woven mesh or nonwoven mesh.

Embodiment 26. The medical device of any one of Embodiments 18 to 25, wherein said knitted mesh, woven mesh or nonwoven mesh includes a combination of said melt extruded, oriented polymeric material fibers and other fibers.

Embodiment 27. The medical device of Embodiment 26, wherein the other fibers are bioabsorbable fibers.

Embodiment 28. The medical device of Embodiment 27, wherein the other fibers bioabsorb more quickly than said melt extruded, oriented polymeric material fibers.

Embodiment 29. The medical device of Embodiment 26, wherein the other fibers are non-bioabsorbable fibers.

Embodiment 30. The medical device of Embodiment 27, wherein the bioabsorbable fibers are selected from the group consisting of polyglactin fibers, polydioxanone fibers, polylactic acid fibers, polylactide fibers, and polylactic acid/glycolic acid copolymer fibers.

Embodiment 31. The medical device of Embodiment 29, wherein the non-bioabsorbable fibers are selected from the group consisting of polypropylene fibers, polyester fibers, polyethylene fibers, acrylic fibers, polyamide fibers, aramid fibers, fluropolymer fibers, and flurocarbon fibers.

Embodiment 32. The medical device of any one of Embodiments 16 to 31, further comprising a decellularized extracellular matrix tissue.

Embodiment 33. The medical device of any one of Embodiments 18 to 31, wherein the knitted mesh, woven mesh or non-woven mesh is connected to at least one sheet of decellularized extracellular matrix tissue.

Embodiment 34. The medical device of Embodiment 33, wherein the knitted mesh, woven mesh or non-woven mesh is sandwiched between a first sheet of extracellular matrix tissue and a second sheet of extracellular matrix tissue.

Embodiment 35. The medical device of any one of Embodiments 32 to 34, wherein the decellularized extracellular matrix tissue comprises a submucosal decellularized extracellular matrix tissue.

Embodiment 36. A method for making a melt extruded, oriented polymeric material fiber, comprising:
melt extruding a polymeric material which is a homopolymer of caprolactone or a copolymer of at least 90% by weight of caprolactone and one or more additional monomers, to form an extrudate;
solidifying the extrudate by cooling the polymeric material; and drawing the extrudate so as to stretch harden the polymeric material. Embodiment 37. The method of Embodiment 36, wherein said drawing step elongates the extrudate by at least 600%.

Embodiment 38. The method of Embodiment 36 or 37, wherein said melt extruding comprises extruding the polymeric material through an opening having a diameter in the range of about 0.2 mm to about 3 mm.

Embodiment 39. The method of any one of Embodiments 36 to 38, wherein said drawing increases the crystallinity of the polymer material.

Embodiment 40. The method of any one of Embodiments 36 to 39, wherein said melt extruding is conducted with the polymeric material at a temperature in the range of about 60° C. to about 140° C.

Embodiment 41. The method of any one of Embodiments 36 to 40, wherein said extrudate has an average diameter in the range of about 0.3 mm to about 4 mm, preferably about 0.3 mm to about 1 mm.

Embodiment 42. The method of any one of Embodiments 36 to 41, wherein said melt extruding is conducted with the polymeric material at a temperature no greater than about 10° C. above its melting temperature and/or wherein said drawing is conducted with the polymeric material at a temperature at least 20° C. below its melting temperature.

Embodiment 43. The method of any one of Embodiments 36 to 42, wherein said drawing is conducted with said polymeric material at a temperature below 40° C., and preferably below 30° C.

Embodiment 44. The method of any one of Embodiments 36 to 43, wherein said drawing is conducted with said polymeric material at a temperature in the range of about 0° C. to about 40° C., preferably about 10° C. to about 30° C.

Embodiment 45. An implantable medical mesh product, comprising:
a mesh structure comprised of woven and/or knit fibers, wherein the fibers include at least one melt extruded, oriented polymeric material fiber, wherein the polymeric material is a homopolymer of caprolactone or a copolymer of at least 90% by weight of caprolactone and one or more additional monomers.

Embodiment 46. The implantable medical mesh of Embodiment 45, wherein the polymeric material has been cold stress hardened, and wherein the at least one melt extruded, oriented polymeric material fiber has a tensile strength of about 450 MPa to about 650 MPa, an elongation at break in the range of 45% to 65%, and an elastic modulus in the range of 750 MPa to 1200 MPa.

Embodiment 47. An implantable medical mesh product of Embodiment 45 or 46, wherein the polymeric material is a homopolymer of caprolactone.

Embodiment 48. An implantable medical mesh product of Embodiment 45, wherein the melt extruded, oriented polymeric material fiber is a fiber according to any one of Embodiments 2 to 15.

Embodiment 49. An implantable mesh product of any one of Embodiments 45 to 48, wherein said mesh structure is enclosed in a package, and wherein the implantable mesh product has been terminally sterilized.

What is claimed is:

1. A melt extruded, oriented polymeric material fiber, wherein the polymeric material is a homopolymer of caprolactone or a copolymer of at least 90% by weight of caprolactone and one or more additional monomers; and further wherein:
   (i) the polymeric material fiber has a tensile strength of about 450 MPa to about 650 MPa; and/or
   (ii) the polymeric material fiber has an elongation at break in the range of 45% to 65%; and/or
   (iii) the polymeric material fiber has an elastic modulus in the range of 750 MPa to 1200 MPa; and/or
   (iv) the tensile strength of the polymeric material fiber, as measured after immersion in phosphate buffered physiological saline for 60 minutes, decreases less than 20% after immersion in phosphate buffered physiological saline for 6 months.

2. The melt extruded, oriented polymeric material fiber of claim 1, wherein the polymeric material has been stress hardened by stretching.

3. The melt extruded, oriented polymeric fiber of claim 1, wherein the polymeric material fiber has an elastic modulus in the range of 750 MPa to 1200 MPa.

4. The melt extruded, oriented polymeric material fiber of claim 1, wherein the polymeric material fiber has a tensile strength in the range of about 500 MPa to about 650 MPa.

5. The melt extruded, oriented polymeric material fiber of claim 1, which has been prepared by a method comprising melt extruding the polymeric material to form an extrudate, allowing the extrudate dwell time to crystallize, and drawing the extrudate.

6. The melt extruded, oriented polymeric material fiber of claim 1, wherein the polymeric material fiber has an average diameter in the range of about 0.01 to about 4 mm.

7. The melt extruded, oriented polymeric material fiber of claim 1, wherein the polymeric material fiber has a crystallinity above 35%.

8. The melt extruded, oriented polymeric material fiber of claim 1, wherein the homopolymer or copolymer is a linear polymer.

9. The melt extruded, oriented polymeric material fiber of claim 1, wherein the tensile strength of the polymeric material fiber, as measured after immersion in phosphate buffered physiological saline for 60 minutes, decreases less than 20% after immersion in phosphate buffered physiological saline for 6 months.

10. The melt extruded, oriented polymeric material fiber of claim 1, wherein the polymeric material fiber has an elongation at break in the range of 45% to 65%.

11. The melt extruded, oriented polymeric material fiber of claim 1, wherein the polymeric material is a homopolymer of caprolactone.

12. The melt extruded, oriented polymeric material fiber of claim 1, wherein the polymeric material is a copolymer of at least 90% by weight of caprolactone and one or more additional monomers.

13. The melt extruded, oriented polymeric material fiber of claim 1, wherein the number average molecular weight of the homopolymer or the copolymer is in the range of about 10000 to about 150000 kDa.

14. The melt extruded, oriented polymeric material fiber of claim 1, which has been sterilized.

15. The melt extruded, oriented polymeric material fiber of claim 14, which has been sterilized by exposure to ethylene oxide gas.

16. A medical device comprising one or more melt extruded, oriented polymeric fibers according to claim 1.

17. The medical device of claim 16, wherein the device is a medical textile, tube, surgical mesh, hernia mesh, breast reconstruction mesh, mastopexy mesh, pericardial patch, anti-adhesion patch, cardiovascular patch, guided tissue regeneration patch, sling, monofilament suture, multifilament suture, ligament repair device, tendon repair device, meniscus repair device, cartilage repair device, nerve guide, stent, vascular graft, or dura repair device.

18. The melt extruded, oriented polymeric material fiber of claim 1, wherein the polymeric material fiber has an average diameter in the range of about 0.1 to 3 mm.

19. The melt extruded, oriented polymeric material fiber of claim 1, wherein the polymeric material fiber has a crystallinity in the range of 35% to 50%.

20. A method for making a melt extruded, oriented polymeric material fiber, comprising:
   melt extruding a polymeric material which is a homopolymer of caprolactone or a copolymer of at least 90% by weight of caprolactone and one or more additional monomers, to form an extrudate;
   solidifying the extrudate by cooling the polymeric material; and
   drawing the extrudate so as to stretch harden the polymeric material
   wherein the polymeric material fiber has a tensile strength of about 450 MPa to about 650 MPa, and/or wherein the polymeric material fiber has an elongation at break in the range of 45% to 65%, and/or wherein the polymeric material fiber has an elastic modulus in the range of 750 MPa to 1200 MPa, and/or wherein the tensile strength of the polymeric material fiber, as measured after immersion in phosphate buffered physiological saline for 60 minutes, decreases less than 20% after immersion in phosphate buffered physiological saline for 6 months.

21. The method of claim 20, wherein said drawing elongates the extrudate by at least 600%.

22. An implantable medical mesh product, comprising:
   a mesh structure comprised of woven and/or knit fibers, wherein the fibers include at least one melt extruded, oriented polymeric material fiber, wherein the polymeric material is a homopolymer of caprolactone or a copolymer of at least 90% by weight of caprolactone and one or more additional monomers; and
   wherein the polymeric material fiber has a tensile strength of about 450 MPa to about 650 MPa, and/or wherein the polymeric material fiber has an elongation at break in the range of 45% to 65%, and/or wherein the polymeric material fiber has an elastic modulus in the range of 750 MPa to 1200 MPa, and/or wherein the tensile strength of the polymeric material fiber, as measured after immersion in phosphate buffered physiological saline for 60 minutes, decreases less than 20% after immersion in phosphate buffered physiological saline for 6 months.

23. The implantable medical mesh product of claim 22, wherein the mesh structure has a tensile strength in the range of about 30 N/cm to about 200 N/cm.

24. The implantable medical mesh product of claim 23, wherein the polymeric material fiber has a tensile strength of about 450 MPa to about 650 MPa.

25. The implantable medical mesh product of claim 22, wherein the mesh structure has a suture retention strength in the range of about 20 N to about 70 N.

26. The implantable medical mesh product of claim 22, wherein the mesh structure has a ball burst strength in the range of about 50 N/cm to about 600 N/cm.

27. The implantable medical mesh product of claim 22, wherein the mesh structure has a density in the range of about 30 to about 100 g/m$^2$.

28. The implantable medical mesh product of claim 22, wherein the mesh structure has an average pore size in the range of about 0.25 µm$^2$ to about 2500 µm$^2$.

29. The implantable medical mesh product of claim 22, wherein the mesh structure is constituted at least 50% by weight of said one or more melt extruded, oriented polymeric material fibers.

30. The implantable medical mesh product of claim 22, wherein said one or more melt extruded, oriented polymeric material fibers are the only fibers of the mesh structure.

31. The implantable medical mesh product of claim 22, wherein the mesh structure includes a combination of said one or more melt extruded, oriented polymeric fibers and other fibers.

32. The implantable medical mesh product of claim 31, wherein said other fibers are bioabsorbable fibers and bioabsorb more quickly than said one or more melt extruded, oriented polymeric material fibers.

* * * * *